US006248569B1

(12) United States Patent
Dunn et al.

(10) Patent No.: US 6,248,569 B1
(45) Date of Patent: Jun. 19, 2001

(54) METHOD FOR INTRODUCING UNIDIRECTIONAL NESTED DELETIONS

(75) Inventors: John J. Dunn, Bellport; Mark A. Quesada, Horseheads; Matthew Randesi, New York, all of NY (US)

(73) Assignee: Brookhaven Science Associates, Upton, NY (US)

(*) Notice: Subject to any disclaimer, the term of this patent is extended or adjusted under 35 U.S.C. 154(b) by 0 days.

(21) Appl. No.: 09/342,353

(22) Filed: Jun. 29, 1999

Related U.S. Application Data

(63) Continuation-in-part of application No. 08/966,958, filed on Nov. 10, 1997, now Pat. No. 5,928,908.

(51) Int. Cl.⁷ .......................... C12N 15/66; C12N 15/63
(52) U.S. Cl. ..................... 435/91.42; 435/320.1
(58) Field of Search ............................. 435/320.1, 91.42

(56) References Cited

U.S. PATENT DOCUMENTS 4,843,003    6/1989    Henikoff et al. .
4,889,799   12/1989    Henikoff et al. .

OTHER PUBLICATIONS

Chang et al., Gene 127: 95–98 (1993).
Life Technologies, GIBCO BRL Products & Reference Guide: pp. 19–14, 19–15, and 19–32 (1997/1998).
Bonaldo et al., Genome Res. 6(9): 791–806 (1996).
Ohara et al., DNA Res. 4(1) : 53–59 (1997).
Suzuki et al., Gene. 200(1–2) : 149–156 (1997).

*Primary Examiner*—Terry McKelvey
(74) *Attorney, Agent, or Firm*—Margaret C. Bogosian

(57) ABSTRACT

Disclosed is a method for the introduction of unidirectional deletions in a cloned DNA segment in the context of a cloning vector which contains an f1 endonuclease recognition sequence adjacent to the insertion site of the DNA segment. Also disclosed is a method for producing single-stranded DNA probes utilizing the same cloning vector. An optimal vector, PZIP is described. Methods for introducing unidirectional deletions into a terminal location of a cloned DNA sequence which is inserted into the vector of the present invention are also disclosed. These methods are useful for introducing deletions into either or both ends of a cloned DNA insert, for high throughput sequencing of any DNA of interest.

33 Claims, 6 Drawing Sheets

```
   1 ATGAGCCATA TTCAACGGGA AACGTCTTGC TCGAGGCCGC GATTAAATTC CAACATGGAT
  61 GCTGATTTAT ATGGGTATAA ATGGGCTCGC GATAATGTCG GGCAATCAGG TGCGACAATC
 121 TATCGATTGT ATGGAAGCC CGATGCGCCA GAGTTGTTTC TGAAACATGG CAAAGGTAGC
 181 GTTGCCAATG ATGTTACAGA TGAGATGGTC AGACTAAACT GGCTGACGGA ATTTATGCCT
 241 CTTCCGACCA TCAAGCATTT TATCCGTACT CCTGATGATG CATGGTTACT CACCACTGCG
 301 ATCCCCGGGA AAACAGCATT CCAGTTATTA GAAGAATATC CTGATTCAGG TGAAAATATT
 361 GTTGATGCGC TGGCAGTGTT CCTGCGCCGG TTGCATTCGA TTCCTGTTTG TAATTGTCCT
 421 TTTAACAGCG ATCGCGTATT TCGTCTCGCT CAGGCGCAAT CACGAATGAA TAACGGTTTG
 481 GTTGATGCGA GTGATTTTGA TGACGAGCGT AATGGCTGGC CTGTTGAACA AGTCTGGAAA
 541 GAAATGCATA AACTTGTGCC ATTCTCACCG GATTCAGTCG TCACTCATGG TGATTTCTCA
 601 CTTGATAACC TTATTTTTGA CGAGGGAAA TTAATAGGTT GTATTGATGT TGGACGAGTC
 661 GGAATCGCAG ACCGATACCA GGATCTTGCC ATCCTATGGA ACTGCCTCGG TGAGTTTTCT
 721 CCTTCATTAC AGAAACGGCT TTTTCAAAAA TATGGTATTG ATAATCCTGA TATGAATAAA
 761 TTGCAGTTTC ATTTGATGCT CGATGAGTTT TTCTAATCAG AATTGGTTAA TTGGTTGTAA
 841 CACTGGCGAG CTCGGATCGC GGCCGTGCCT ACCTTAGGAC CGTTATAGTA GGGATAACAG
 901 GGTAATGGCG CCGACGTCGG CCGAGGCCCG GGCGTTTAAA CATTTAAATG TCGACATACG
 961 ATTTAGGTGA CACTATAGAA CTCTAATACG ACTCACTATA GGGAATTTGG CCCTCGAGGC
1021 CAAGAATTCC CGACTACGTA GTCGGGGATC CATGATCATG GCGGCCGCAA GCTTAATTAA
1081 CCTGTAGCT TATTCCCTTT AGTGAGGGTT AATTTAGCT TGGCACTGGC CGTCGTTTTA
1141 CAACGTCGTG ACTGGGAAAA CCCTGTTAAC CGGCGCGCCA CGGCGTACCCA TAATACCCAT
1201 AATAGCTGTT TGCCATCGCG TATGCATGTCC ACGTGTCC ACGTCTTTTA ATAGTGGACT
1261 CTTGTTCCAA ACTGGAACAA CACTCGGATC GATCCGGGGC GCACCGTGGG AAAAACTCCA
1321 GGTAGAGGTA CACACGCGA TAGCCAATTC AGAGTAATAA ACTGTGATAA TCACCCCTCA
1381 TCAATGATGA CGAACTAACC CCCGATATCA GGTCACATGA CGAAGGGAAA GAGAAGGAAA
1441 TCAACTGTGA CAAACTGCCC TCAAATTTGG CTTCCTTAAA CAAAACTGTG AATTACAGTT CAAAAGTAT
1501 GAGAAAATCC ATGCAGGCTG AAGGAAACAG CAAACTGTG ACACCCTCAG CTCAGTAGGT
1561 CAGAACAAAT GTGACGAACC ACCCTCAAAT CTGTGACAGA TAACCCTCAG ACTATCCTGT
1621 CGTCATGGAA GTGATATCGC CATCCTCTTC TACGATATGA GTCGTCTGGC GGCCTTTCTT
1681 TTTCTCAATG TATGAGAGGC GCATTGGAGT TCTGCTGTTG ATCTCATTAA CACAGACCTG
1741 CAGGAAGCGG CGGCGGAAGT CAGGCATACG CTGGTAACTT TGAGGCAGCT GGTAACGCTC
1801 TATGATCGAC TCGATTTTCA GAGACGCGAT GCCTGAGCCA TCCGGCTTAC GATACTGACA
1861 CAGGGATTCG TATAAACGCA TGGCATACGG ATTCGTGATT TCTTTTGTTT CACTAAGCCG
1921 AAACTGCGTA AACCGGTTCT GTAACCCGAT AAGAAGGGA ATGAGATATG GGTTGATATG
1981 TACACTGTAA AGCCCTCTGG AGCACGTGTG CGCACGTTTG ATAAACCAAG GAAAAGATTC
2041 ATAGCCTTTT TCATCGCCGC ATCCTCTTC AGGGCGATAA AAAACCACTT CCTTCCCCGC
2101 GAAACTCTTC AATGCCTGCC GTATATCCTT ACTGCCTTCC GCAGAGGTCA ATCCGAATAT
2161 TTCAGCATAT TTAGCAACAT GGATCTCGCA GATACCGTCA GATACCGTA TGTTCCTGTA GGGTGCCATC
```

```
2221  AGATTTCTG ATCTGTCAA CGAACAGATA CAGCATACGT TTTTGATCCC GGGAGAGACT
2281  ATATGCCGCC TCAGTGAGGT CGTTTGACTG GACGATTCGC GGGCTATTTT TACGTTTCTT
2341  GTGATTGATA ACCGCTGTTT CCGCCATGAC AGATCCATGT GAAGTGTGAC AAGTTTTTAG
2401  ATTGTCACAC TAAATAAAA AGAGTCAATA AGCAGGGATA ACTTTGTGAA AAAACAGCTT
2461  CTTCTGAGGG CAATTTGTCA AAGGGTAAG GGCAATTTGT CACAGACAGG ACTGTCATTT
2521  GAGGTGATT TGTCACACTG TCTAAAAAA TTGTCACAAC ACCTTCTCTA GAACCAGCAT
2581  GGATAAAGGC CTACAAGGCG TCTAAAAAA GAAGATCTAA AAACTATAAA AAAAATAATT
2641  ATAAAATAT CCCCGTGAT AAGTGGATAA CCCCAAGGGA AGTTTTTTCA GGCATCGTGT
2701  GTAAGCAGAA TATATAAGTG CTGTTCCCTG GTGCTTCCTC GCTCACTCGA AATTCCCGGG
2761  GATAGCTTTA TGCTTGTAAA CCGTTTTGTG AAAAAATTTT TAAAATAAAA AAGGGACCT
2821  CTAGGGTCCC CAATTAATTA GTAATATAAT CTATTAAAGG TCATTCAAAA GGTCATCCAC
2881  CGGATCAATT CCCCTGCTCG CGCAGGCTGG GTGCCAAGCT CTCGGGTAAC ATCAAGGCCC
2941  GATCCTTGGA GCCCTTGCCC TCCCGCACGA TGATCGTGCC GTGATCGAAA TCCAGATCCT
3001  TGACCCGCAG TTGCAAACCC TCACTGATCC GATTCATTAA TGCAGCTGGC ACGACAGGTT
3061  TCCCGACTGG AAAGCGGGCA GTGAGCGCAA CGCAATTAAT GTGAGTTAGC TCACTCATTA
3121  GGCACCCCAG GCTTTACACT TTATGCTTCC GGCTCGTATG TTGTGTGGAA TTGTGAGCGG
3181  ATAACAATTT CACACAGGAA ACAGCTATGA CCATGATTAC GCCAAGCGCG GTACCTGTCG
3241  CGGCAACGCG CTAACAGACG TAGTAAGAAC CACCAGCATT GTAATGCTGG CTAAAGTCAC
3301  TTTCCTGAGC TGTATAACGA TGAGCGATTT TACTTTTTCT GGCTATGAAT TGGCCTGCTT
3361  TGTAACACAC TCCGGTCTAT CCCGTAGCGC CGGGCATATC CTGTCGCAAT GTGCAAATCT
3421  CGCGGCAACA ACCAGTGAAT ACTTCATTCA CAAGCCTCAC CGCCTGATCG CGGCAGAAAC
3481  TGGTTATAGC CAATCAACCG TCGTTCGTGC TCGTAAACA GCTGAAACA AAGGTATCCT
3541  GTCGTGAGAG ATTGTTATCG GCGATCACCG GCAGATCGC TGAACGTGC GCTAACCTGT ACCGGTTAC
3601  ACCATCCTTT TTGGCCTTCG CACAACAAGC CAAAATGCG CTGATAGAAA GCAAATTAAA
3661  GATCTCTTCA GCGGCAACCA AGTTAAAGC TGTTCTCGCT AAGACATTGG CTTTATTTAA
3721  TTTTTTATCC ACACCCCAT GTCAAAATGA TACCCCCTCC CCCTGTCAGG ATGACGTGGC
3781  AATAAAGAAT AAGAAGTCAC AAGTTAAAAA AACAAAAAGA TCAGTTTCCG GCGGTGCCGG
3841  AACAACCAGC CTCAAAAAAT TGACTTCATG GATCGCTAAG GCAAAAGCAA AGGCTGACAA
3901  TCTGCGGTTA TCCAAAAAC GCACTCAAAA ACATGAGTTC AAGCAGAAAG TAGAGGCGGC
3961  TGCGCGGAAA TATGCTTACC TGAAGAACAA GCGTTCGCCT GATATTGGCG GGATATCAAA
4021  CTTCGATAAC CTACGCCATT GCATGACGGT AACGAAGCT CTTAATGCGG TTTTAGCCAA
4081  AAATAAGAT AACGAACAAT GGGTATACC GCAGGATTC GGCAGAAAC AGAGGGTAAT GAATTGCTCT
4141  AATTATACCC ATGCACATCT TCAACACCTC TAGTTTGCCA TGAGGCAAAC TCATAGGTGT
4201  CCTGTAAGA GTGACACTGT CCAAAACTG GACGCCCCAT TATTGCAATT AATAACAAC
4261  TAACGGACAA TTCTACCTAA CAATAAGTGG AGTTGCGGG GCCCGGATC CGCTAGCAAA
4321  GCCACGTTGT GTCTCAAAAT CTCTGATGTT ACATGCACA AGATAAAAT CGTAGCATCAT ATATCATCAT
4381  GAACAATAAA ACTGTCTGCT TACATAAACA GTAATACAAG GGGTGTT
```

METHOD FOR INTRODUCING UNIDIRECTIONAL NESTED DELETIONS

This application is a continuation-in-part of U.S. application Ser. No. No. 08/966,958, filed Nov. 10, 1997, now U.S. Pat. No. 5,928,908, the contents of which are incorporated herein by reference.

This invention was made with Government support under contract number DE-AC02-98CH10886, awarded by the U.S. Department of Energy. The Government has certain rights in the invention.

BACKGROUND OF THE INVENTION

DNA sequencing is a fundamental research tool with wide-ranging applications. A common approach to DNA sequencing involves the subcloning of a large DNA fragments as smaller, overlapping fragments, the sequences of which are subsequently determined using the dideoxynucleotide chain termination approach (Sanger and Coulson, *Proc. Natl. Acad. Sci. USA* 74: 5463 (1977)).

Subcloning, and the restriction mapping required to efficiently subclone fragments, is a time consuming and labor intensive process. However, given the limitations associated with the amount of sequence which can be determined from a single extension reaction, it is necessary to initiate new sequencing reactions at a distance of about every 300–400 base pairs along a fragment, the sequence of which is to be determined.

One alternative to the subcloning approach is described by Henikoff et al. in U.S. Pat. Nos. 4,843,003 and 4,889,799. More specifically, Henikoff et al. describe a method in which a vector containing a DNA sequence of interest is linearized by digestion at two restriction endonuclease recognition sites, one generating a 5' overhang and the other a blunt end or 3' overhang. Timed digestion with *E. coli* Exo III from the 5' overhang, followed by treatment with a single-strand-specific nuclease generates a nested array of deletions. Unfortunately, this technique also is limited by the need for conveniently located restriction endonuclease recognition sequences.

An alternative to the approach described above was outlined by Chang et al. (Gene 127: 95 (1993)). Chang et al. describe a method in which a single-stranded nick is introduced at a position adjacent to the site at which a DNA fragment having a sequence which is to be determined is inserted in a cloning vector. The nick in the DNA is then extended under controlled digestion conditions to produce a single-stranded gap. The single-stranded gap is then treated with a nuclease which specifically digests single-stranded DNA, thereby producing a deletion within the DNA sequence of interest.

Chang et al. specifically report that the single-stranded nick in the DNA of interest cannot be expanded by treatment with *E. coli* Exo III. Given the fact that Exo III is a well-understood, relatively inexpensive enzyme, Chang et al. note that this is an unfortunate finding (page 96, column 2). The development of protocols which would enable the use of Exo III in such a DNA sequencing strategy would represent an important improvement in the art.

In the last decade significant effort and resources have been devoted to the sequencing of entire genomes and expressed sequences of various organisms. The human genome specifies an estimated 60,000 to 100,000 proteins and the mouse genome a comparable number. Large-scale single-pass sequencing of cDNAs has been very successful in gene identification. The current version of UniGene, the NCBI clustering of known genes and expressed sequence tags, contains more than 60,000 clusters of human expressed sequences, more than 8,000 of which correspond to known genes. The corresponding collection from mouse contains more than 15,000 clusters, almost 4,500 of which correspond to known genes. Such efforts rely on normalized cDNA libraries from a variety of tissues.

Although cDNA clones need not be full length to provide valuable information by single-pass sequencing from their ends, the complete sequence of full-length cDNA clones provides the coding sequences for the proteins and, by comparing with genome sequence, the locations of introns. Full-length clones are also needed for expressing proteins for functional analysis. Several efforts are underway to generate normalized cDNA libraries that will be enriched for full-length clones (Bonaldo et al., *Genome Res.* 6(9): 791–806 (1996); Ohara et al., *DNA Res.* 4(1): 53–9 (1997); Suzuki et al., *Gene.* 200(1–2): 149–56 (1997)).

Ultimately, sequences of tens of thousands of full-length cDNAs from human and mouse will be needed for understanding the functions of human mRNAs and proteins. The variety of uses to which these sequences will be put requires that they be determined at the highest possible accuracy, certainly at or better than the 99.99% accuracy required of genome sequences. Obtaining the complete sequence of these cDNA clones, most of which will range in length from a few hundred to several thousands of base pairs, is not particularly efficient with the shotgun sequencing procedures currently used for high-throughput sequencing of large-insert genomic clones. Inserts must first be purified from vector fragments and then shotgun libraries must be prepared either from the insert itself (Ohara et al., *DNA Res.* 4(1): 53–9 (1997)) or from mixtures of inserts from different clones ligated together (Yu et al., Genome Res. 7(4): 353–8 (1997)). Primer walking may be a viable alternative, particularly for shorter clones: the cost of the many primers needed for primer walking has decreased markedly, whether obtained commercially, produced locally with high capacity synthesizers (Lashkari et al., *Proc. Natl. Acad. Sci. USA* 92(17): 7912–5 (1995); Rayner et al., *Genome Res.* 8(7): 741–7 (1998)), or generated by ligation from a hexamer library (Dunn et al., *Anal Biochem.* 228(1): 91–100 (1995)). Other possible approaches include sequencing by priming from the ends of an appropriately spaced collection of insertion elements selected after random insertion events (Strathmann et al., *Proc. Natl. Acad. Sci. USA* 88(4): 1247–50 (1991); Berg et al., Gene. 113(1): 9–16 (1992); Martin et al., *Proc. Natl. Acad. Sci. USA* 92(18): 8398–402 (1995); York et al., *Nucleic Acids Res.* 26(8): 1927–33 (1998)) or the use of nested deletions to generate sequencing substrates (reviewed in Ausubel, F. M., R. Brent, R. E. Kingston, D. D. Moore, J. G. Seidman, J. A. Smith, and K. Struhl. 1995. *Current Protocols in Molecular Biology, vol.* 1. Wiley, New York).

Sequencing highly repeated regions of human DNA, such as found near telomeres and centromeres, presents its own set of difficulties. Sequencing by producing nested deletions is a viable solution for sequencing such difficult DNA sequences.

Several procedures have been developed to generate nested deletions (Henikoff, S., *Gene.* 28(3): 351–9 (1984); Chang et al., *Gene.* 127(1): 95–8 (1993); Kawarabayasi et al., *DNA Res.* 1(6): 289–96 (1994); Shearer, G., Jr., *Anal Biochem.* 223(1): 105–10 (1994); Hattori et al., *Nucleic Acids Res.* 25(9): 1802–8 (1997); Ren et al., *Anal Biochem.* 245(1): 112–4; Fradkov et al., *Anal Biochem.* 258(1): 138–41 (1998)).

Vectors currently used for preparing and normalizing cDNA libraries are multi-copy (Soares et al., *Proc. Natl. Acad. Sci. USA* 91(20): 9228–32 (1994); Bonaldo et al., *Genome Res.* 6(9): 791–806 (1996); Ohara et al., *DNA Res.* 4(1): 53–9 (1997)). This may be convenient for obtaining the substantial amounts of DNA needed for normalization procedures or for preparing hybridization arrays with the resulting clones, but longer clones, and clones that can express proteins, are typically more stable in single-copy vectors, such as those based on the F or Pi lysogenic replicons (Shizuya et al., *Proc. Natl. Acad. Sci. USA* 89(18): 8794–7 (1992); Ioannou et al., *Nat. Genet.* 6(1): 84–9 (1994)). Thus, a single-copy vector might be expected to provide a more uniform representation of full-length cDNA clones than a multi-copy one.

Although a tremendous amount of progress has been made, the development of more efficient and accurate methods for high throughput sequencing are needed to further expedite the process.

SUMMARY OF THE INVENTION

The present invention relates, in one embodiment, to a method for the introduction of unidirectional deletions in a cloned DNA segment. More specifically, the method comprises providing a recombinant DNA construct comprising a DNA segment of interest inserted in a cloning vector, the cloning vector having an f1 endonuclease recognition sequence adjacent to the insertion site of the DNA segment of interest. The recombinant DNA construct is then contacted with the protein pIT encoded by gene II of phage f1 thereby generating a single-stranded nick. The nicked DNA is then contacted with *E. coli* Exonuclease III thereby expanding the single-stranded nick into a single-stranded gap. The single-stranded gapped DNA is then contacted with a single-strand-specific endonuclease thereby producing a linearized DNA molecule containing a double-stranded deletion corresponding in size to the single-stranded gap. The DNA treated in this manner is then incubated with DNA ligase under conditions appropriate for ligation.

In another embodiment, the invention relates to methods for producing single-stranded DNA probes. In this embodiment, single-stranded gapped DNA, produced as described above, is contacted with a DNA polymerase in the presence of labeled nucleotides to fill in the gap. This DNA is then linearized by digestion with a restriction enzyme which cuts outside the DNA segment of interest. The product of this digestion is then denatured to produce a labeled single-stranded nucleic acid probe.

Another aspect of the present invention is a DNA cloning vector for generating unidirectional deletions in a cloned insert. The vector comprises a cloning region for insertion of a DNA sequence having a first and second terminus; recognition sequences for a first and a second Exo III resistance cutter adjacently located at discrete positions on a first side of the cloning region, the first Exo III resistance cutter recognition sequence being located between the cloning region and the second Exo III resistance cutter recognition sequence; recognition sequences for a set of Exo III sensitizing cutters located between the first Exo III resistance cutter recognition sequence and the cloning region; and an f1 endonuclease recognition sequence adjacently located on the second side of the cloning region. In a preferred embodiment, the DNA cloning vector further comprises recognition sequences for a second set of Exo III sensitizing cutters located between the f1 endonuclease recognition sequence and the cloning region. In another embodiment, the DNA cloning vector further comprises a recognition sequence for a third Exo III resistance cutter located between the f1 endonuclease recognition sequence and the recognition sequences for the second set of Exo III sensitizing cutters. The DNA cloning vector is preferably a single-copy vector for generating normalized full-length cDNA libraries. Other useful features of the DNA cloning vector include a Pi lytic replicon which is under the control of an inducible promoter, and one or more sequencing primer binding sites. An optimal vector, PZIP, is disclosed.

The present invention also relates to methods for introducing unidirectional deletions in a terminal location of a cloned DNA sequence which is inserted into the vector of the present invention. These methods are useful for introducing deletions into either or both ends of a cloned DNA insert, for high throughput sequencing of any DNA of interest. Preferably, the cloned DNA is a cDNA from a cDNA library.

BRIEF DESCRIPTION OF THE DRAWINGS

FIG. 3 lists the sequence of one strand, 5' to 3', of the entire pZIP vector, SEQ ID NO: 2. Nucleotide 1 of the sequence corresponds to the first nucleotide of the first codon of the kanamycin resistance marker (kanamycin phosphotransferase) in the pZIP vector, diagrammed in FIG. 2.

DETAILED DESCRIPTION OF THE INVENTION

Figure 1A:
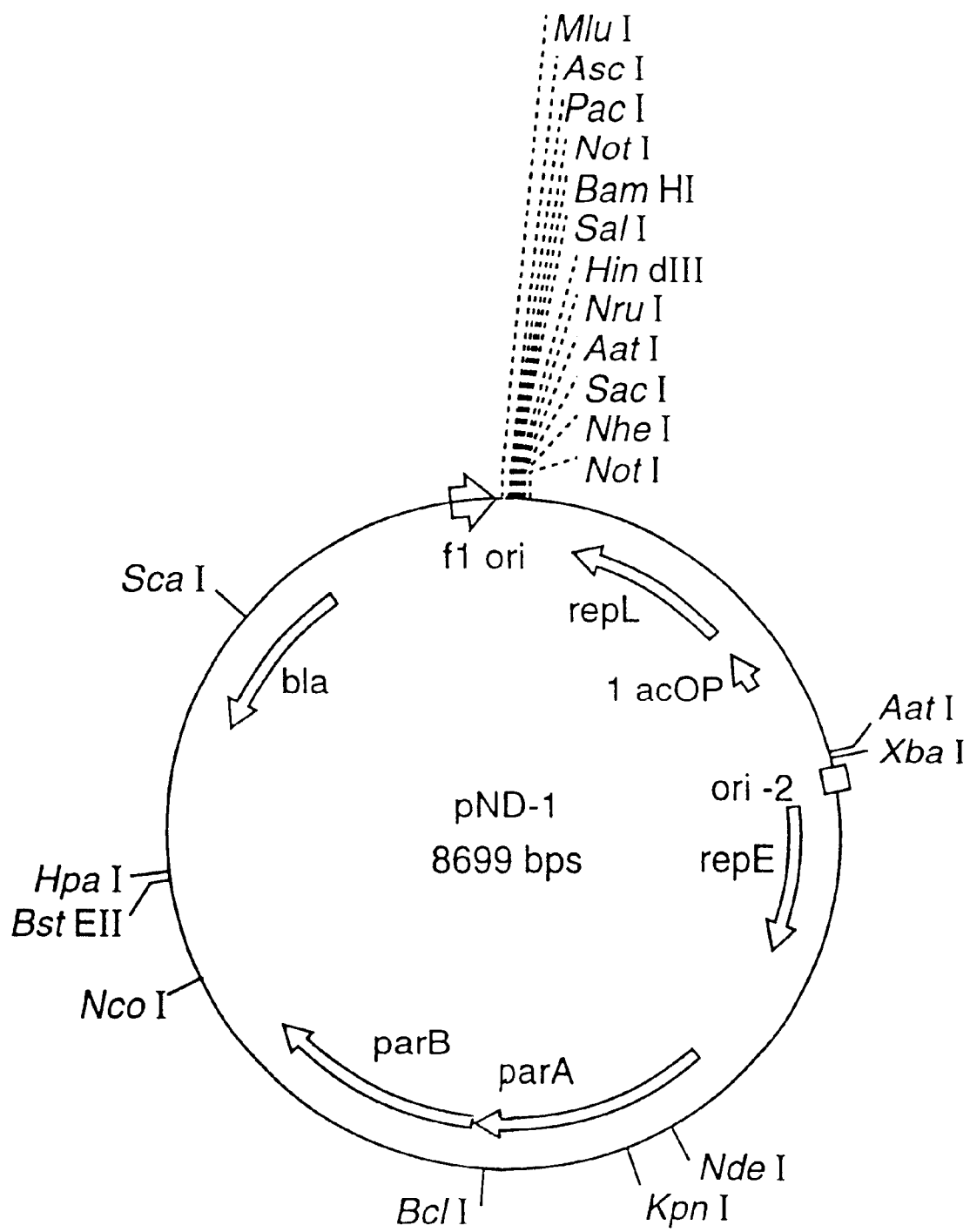
FIG. 1 is a diagrammatic representation of the vectors pND-1 and pND-2.
Figure 1B:
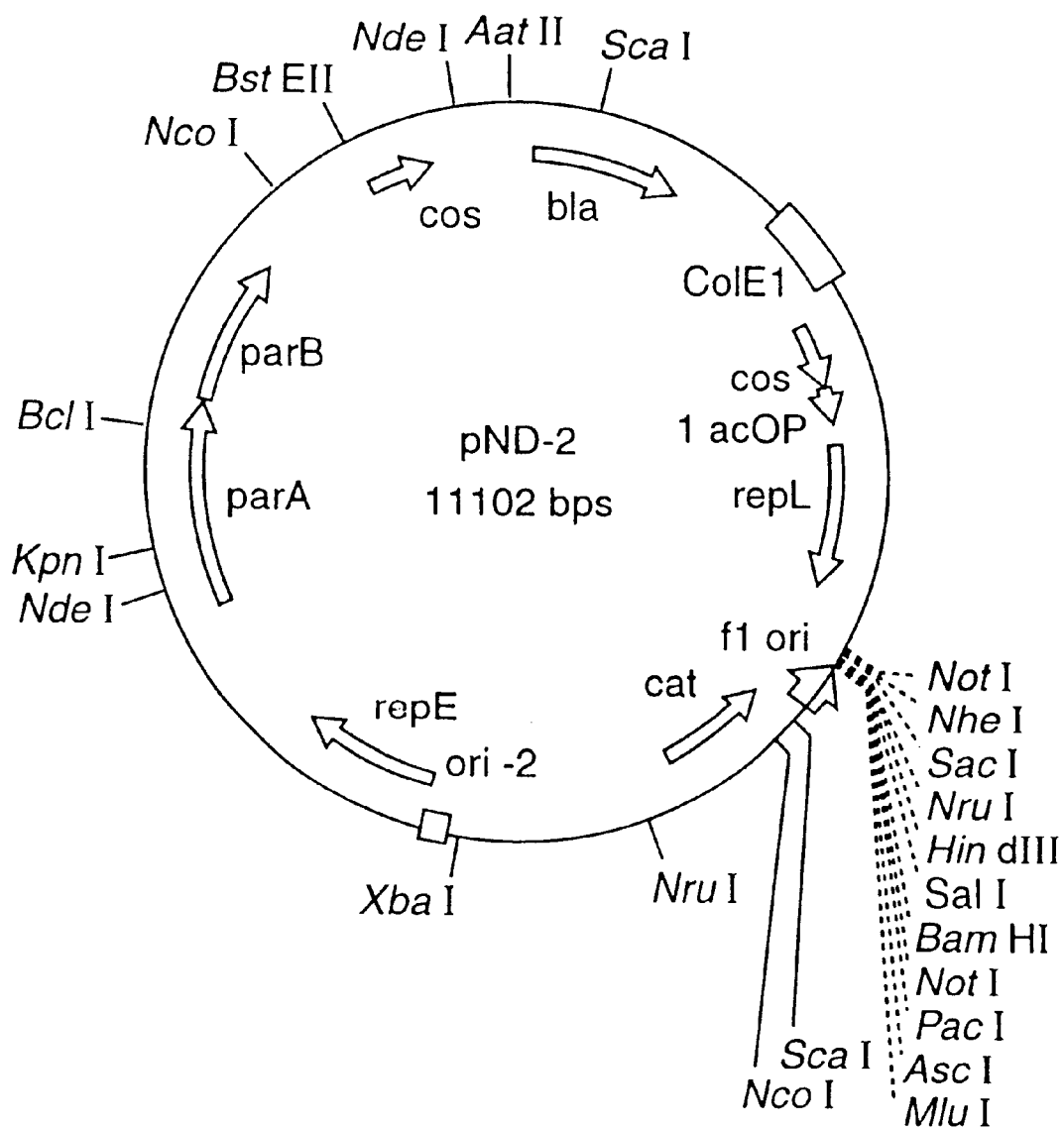

The subject invention relates to a universal method for generating a nested set of unidirectional deletions within a cloned DNA fragment. The method is applicable to a variety of molecular biological applications including, for example, DNA sequencing and the production of labeled single-stranded probe sequences. The method is based on the surprising discovery that *E. coli* Exo III is capable of extending a single-stranded nick, introduced into double-stranded DNA by the phage f1, gene II product, into a gapped structure.

As discussed in the background section, the prior art teaches that *E. coli* Exo III is incapable of extending a nick in double-stranded DNA, introduced into double-stranded DNA by the phage f1, gene II product, into a gapped structure. As shown in the experiments described below, this teaching is incorrect.

More specifically, Applicants produced a recombinant DNA construct comprising a DNA segment of interest inserted in a cloning vector, the cloning vector having an f1 endonuclease recognition sequence adjacent the insertion site of the DNA segment of interest. The recombinant DNA construct was contacted with the protein pII encoded by gene II of phage f1 thereby generating a single-stranded nick. This digestion was carried out in the presence of the divalent cation Mn?'. The nicked DNA was then treated with *E. coli* Exo III thereby expanding the single-stranded nick into a single-stranded gapped structure. The Exo III digestions were carried out under timed conditions to generate molecules having singled-stranded gaps of varying sizes.

The single-stranded gapped DNA is then treated with a single-strand-specific endonuclease (e.g., mung bean or Si endonuclease) thereby producing a linearized DNA molecule containing a double-stranded deletion corresponding in size to the single-stranded gap. The DNA containing the double stranded deletion is then incubated with DNA ligase under conditions appropriate for ligation. In a preferred embodiment of the present invention, dNTPs and DNA polymerase are included in the ligation reaction to blunt any ragged ends which may have been produced in the deletion process.

When used in connection with DNA sequencing protocols, this method of producing unidirectional nested deletions can be fine-tuned to result in an ordered set of nested deletions whose ends are separated by about 300–400 base pairs. This allows rapid sequencing across one strand of a cloned DNA fragment using a universal primer. Any gaps remaining after this process can be closed by primer walking on the original clone. Even highly repeated DNA can easily be assembled correctly, knowing the relative locations of the sequences obtained. As shown in the Exemplification section which follows, the disclosed method has been employed to determine the DNA sequence of cloned fragments at least as large as 17 kb. It is reasonable to postulate an upper limit of 40–50 kb for the size of cloned fragments which can be sequenced in this manner.

Two specific vectors (pND-1 and pND-2) were used in connection with the experiments described in Section I of the Exemplification below. Both are single-copy amplifiable vectors stably maintained at low copy number by the F replication and partitioning functions and can be amplified from an IPTG-inducible Pi lytic replicon to prepare DNA. A synthetic version of the phage f1 origin of replication is located a short distance upstream of the multiple cloning site. Vector pND-1 was used primarily for obtaining clones by transformation or electroporation. Vector pND-2 has phage lambda cos sites that allow efficient cloning of 30–40 kb fragments in a lambda packaging system.

Although the demonstration below was accomplished with the two low copy number vectors, one of skill in the art will recognize that the teachings of the present invention apply to any type of cloning vector.

Reaction conditions have been defined where purified f1 gene 2 protein efficiently introduces a strand-specific single nick in the f1 origin sequence with very little rejoining. Large amounts of stable gene 2 protein are obtained using recombinant DNA production techniques. The Exo III digestion is highly synchronous and processive, and the deletion lengths are proportional to incubation time. In one embodiment, to prevent undeleted DNA from giving rise to clones, treated DNA is digested with one of several restriction enzymes whose 8-base recognition sequences lie between the fi origin and the cloning site. Nested deletion clones are then obtained by electroporation.

Pooling samples from several different times of Exo III digestion before subsequent treatment generates a good distribution of deletion clones. Growth and amplification of randomly selected clones in 1 ml of medium in 96-well format followed by a simple DNA preparation protocol provides ample DNA for analyzing deletion length by gel electrophoresis and for DNA sequencing reactions. Imaging and sizing software is now being tested for automated selection of an appropriate set of deletions for sequencing.

In addition to the method for producing nested deletions discussed above, the invention also relates to a method for producing labeled single-stranded DNA probes. The method for producing labeled single-stranded DNA probes is essentially identical to the method described above for producing nested deletions, through the DNA gapping step. However, rather than digesting single-stranded DNA with an endonuclease following the gapping step, the gap is instead filled in by a DNA polymerase in the presence of labeled dNTPs. The molecule is then linearizing by digestion with a restriction enzyme which cuts outside the DNA segment of interest. The product is then denatured (e.g., by heating) to produce a labeled single-stranded nucleic acid probe.

Another aspect of the present invention is a DNA cloning vector for generating unidirectional deletions in a cloned insert, the deletions being introduced into either terminus, or alternatively both termini of the insert. Similar to the above described vectors pND-1 and pND-2, the present vector has a cloning region for insertion of a cloned insert, and an f1 endonuclease recognition sequence located directly adjacent to the cloning region. In addition, it has recognition sites for endonucleases which produce Exo III resistant ends, and also sites for endonucleases which produce Exo III sensitive ends, located at discrete positions on either side of the cloning region. The specific locations of these recognition sequences with respect to one another allows for rapid introduction of unidirectional deletions into either or both termini of any inserted DNA sequence. Use of the vector of the present invention by the methods described below, produces a range of deleted inserts into a cloned DNA sequence of interest. Use of sequencing primers specific for the vector sequences enables sequencing across the deleted inserts, to generate sequence corresponding to the entire inserted DNA, without the need for subcloning or synthesizing new primer oligonucleotides.

Although the vector is circular, description of the vector is facilitated by conceptualizing the cloning region as flanked by two directly adjacent regions of vector sequence, referred to herein as a first side and a second side. The directional location of the first and second side within the vector is arbitrary, the importance lying within the opposition of the components of the two sides from one another with respect to the cloning region. Specific recognition sequences are incorporated into the vector sequence that constitutes the first side and second side of the cloning region. Recognition sequences for a first and a second restriction enzyme which produces Exo III resistant ends, designated herein as an Exo III resistance cutter, are adjacently located at discrete positions on the first side of the cloning region. These two recognition sequences are positioned such that the first Exo III resistance cutter recognition sequence is located between the cloning region and the second Exo III resistance cutter recognition sequence. Positions between the first Exo III resistance cutter recognition sequence and the cloning region, are distinct recognition sequences for a set of restriction enzymes which produce Exo III sensitive ends, referred to herein as Exo III sensitizing cutters. The term "set" as used herein refers to one or more. An f1 endonuclease recognition sequence is incorporated into the vector sequences located within the second side of the cloning region.

In a preferred embodiment, the cloning region is a multiple cloning region (MCR) which contains several unique sites for both shotgun and directional cloning of any DNA of interest. The direction of insertion of the DNA sequence into the vector, with respect to the first side and the second side of the cloning region, defines a first and a second terminus of the DNA sequence. The terminus which is inserted directly adjacent to the first side of the cloning region is defined herein as the first terminus, the terminus which is inserted directly adjacent to the second side of the cloning region, is defined herein as the second terminus.

The first and second recognition sequences for Exo III resistance cutters are for two distinct endonucleases which generate cut ends which cannot serve as substrate for digestion with E. coli Exo III. Inclusion of additional sequences for other Exo III resistance cutters in this region may be useful for manipulation of DNA inserts which contain one or more of these recognition sequences. In a preferred embodiment, one or both of the Exo III resistance cutters are extremely rare cutting intron encoded endonucleases (e.g. I-CeuI, I-SceI, and PI-PspI). Digestion with any of these endonucleases produces a four-base 3' overhang which is not susceptible to Exo III digestion.

The recognition sequences for a set of Exo III sensitizing cutters, located between the first Exo III resistance cutter recognition sequence and the cloning region, are a compilation of distinct recognition sequences for one or more restriction enzymes which produce Exo III sensitive ends. In a preferred embodiment, one or more of the Exo III sensitizing cutters are rare 8-base recognition endonucleases which generate ends that serve as template for E. coli Exo III. Without limitation, such endonucleases include SrfI, PmeI, SwaI, NotI, PacI, and AscI.

As described above, the f1 endonuclease recognition sequence is a nicking site for the phage f1 protein, gpII. gpII can be used to initiate f1 rolling circle DNA replication. One of skill in the art will recognize the inherent limitations of proximity of the various recognition sequences to each other and to the cloning region, required for adequate function in the present invention as described herein.

In a preferred embodiment, the vector is a single-copy vector for generating normalized full-length cDNA libraries. Preferably, the vector additionally has a Pi lytic replicon (repL) which is under the control of an inducible promoter, such as the Lac operon (lacOP) which is inducible with IPTG. This allows controlled amplification of the plasmid which is useful for generation of large amounts of plasmid, or plasmid with insert. In an alternate embodiment, the DNA cloning vector is a high copy number vector. Inclusion of one or more markers which facilitate subcloning and propagation of the vector (e.g. antibiotic resistance) is also preferred.

Substantial benefits may also be obtained by inclusion of additional recognition sequences into the cloning vector which facilitate generation of deletions or identification of deleted clones. In one embodiment, a sequence for a third Exo III resistance cutter is located on the second side of the cloning region, between the f1 endonuclease recognition sequence and the cloning region. In another embodiment, recognition sequences for a second set of Exo III sensitizing cutters are located on the second side of the cloning region, between the f1 endonuclease recognition sequence and the cloning region. Potential sites for Exo III sensitizing cutters are described above. Preferably, the Exo III sensitizing cutters of the second set are distinct from those of the first set. A DNA cloning vector which contains both the third Exo III resistance cutter site and recognition sequences for the second set of Exo III sensitizing cutters, preferably has the third Exo III resistance cutter sequence located between the f1 endonuclease recognition sequence and the recognition sequence for the second set of Exo III sensitizing cutters.

The DNA cloning vector of the present invention, preferably has promoter sites for SP6, T7, and T3 RNA polymerase flanking the cloning region, as in the pZIP vector, described below. These sites can be used for priming sequencing reactions which generate sequence of the cloned insert, or alternatively for generating sense or anti-sense RNA transcripts from the cloned insert template. The pzip vector, diagrammed in FIGS. 2 and 3 incorporates all of the above described features, and has been optimized for function. The sequence of pZIP is listed in SEQ ID NO: 2. pZIP is a single-copy vector which is useful for making normalized full-length cDNA libraries and also for generating nested deletions from either end of a cloned insert. Tests with human genomic DNA have been successful for stably cloning and propagating DNA fragments as large as 15 kb, well within the range expected for most full-length cDNAs. Although full-length cDNAs in existing cDNA libraries can be transferred to a vector for generating deletions for sequencing, actually generating a cDNA library initially in a vector that is suitable for making deletions is a far more efficient approach.

The region of PZIP which contains the cloning region and flanking recognition sequences described above, are shown in FIG. 4. One of skill in the art will recognize that another suitable cloning vector which contains this region inserted can be used in the methods for introducing unidirectional deletions, described below.

Upon introduction of a DNA sequence of interest into the cloning region of the DNA cloning vector described directly above, unidirectional deletions are generated from either end of the DNA sequence of interest. Deletions in the second terminus (the terminus of the DNA sequence which is inserted directly adjacent the f1 origin), are similar to methods described above. Briefly, a single-stranded nick is introduced with protein pII. This is carried out in the presence of the divalent cation $Mn^{2+}$. Exo III is then contacted to the nicked DNA to generate a single stranded gap from the single-stranded nick. The DNA with the single stranded gap is then treated with a single-strand-specific endonuclease, which removes existing single stranded DNA overhangs, to produce a linearized DNA molecule containing a double-stranded deletion corresponding in size to the single-stranded gap. The linearized DNA molecule is then recircularized with ligase.

In a preferred embodiment, the method is performed using a cloning vector which contains a recognition sequence for a third Exo III resistance cutter, located between the f1 endonuclease recognition sequence and the cloning region. This extra recognition sequence is useful for eliminating any DNA constructs which are undigested by Exo III, and therefore do not have unidirectional deletions in the second terminus of the inserted DNA. Such background vectors are selectively linearized by digestion with the third Exo III resistance cutter, the site for which is eliminated by introduction of the desired deletion. Because linearized DNA transforms bacteria with extremely low efficiency, this digestion counterselects against intact parent vector constructs.

Inclusion of a second set of Exo III sensitizing cutters located between the third Exo III resistance cutter recognition sequence and the cloning region, provides for an alternate method of generating unidirectional deletions in the second terminus of a DNA insert. The vector construct is digested with any member of the second set of Exo III sensitizing cutters to produce two ends which are susceptible to Exo III digestion. Digestion with the third Exo III resistance cutter prior to Exo III digestion, produces an Exo III resistant end prevents Exo III digestion into the vector, but allows single stranded digestion by Exo III in the 3'–5' direction into the second terminus of the cloned insert. This is then followed up by digestion with single-strand-specific endonuclease and then ligation, described in more detail below, to produce the desired double stranded deletion.

Deletions in the first (opposite) terminus of the inserted DNA sequence, are made by a series of endonuclease digestions which linearize the recombinant DNA construct at a site in the vector located directly adjacent the first terminus of the inserted DNA. The series of digestions generates one Exo III sensitive end which corresponds to the end directly adjacent the first terminus of the inserted DNA sequence, and one Exo III insensitive end which protects the rest of the vector sequences from Exo III digestion. The unique vector design allows this to be accomplished by more than one method, described below.

The desired deletion is introduce into a linearized construct which has one Exo III sensitive end (directly adjacent the cloned insert) and one Exo III resistant end by contacting the construct with Exonuclease III of *E. coli* (Exo III), under conditions appropriate for digestion. The Exo III thereby digests into the cloned insert but not into the vector, digesting one strand of the Exo III sensitive end in the 3' to 5' direction to generate a single-stranded deletion in the terminus of the inserted DNA. The construct which is produced is then contacted with a single-strand-specific endonuclease (e.g. Si endonuclease or mung bean endonuclease) under conditions appropriate for digestion. The action of the single-strand-specific endonuclease generates a double-stranded deletion corresponding in size and location to the single-stranded deletion produced by the Exo III digestion. The DNA molecule is then ligated by contacting with DNA ligase under the appropriate conditions, to recircularize the molecule.

The above described linearized vector which has an Exo III sensitive end near the insert's first terminus, and an Exo III resistant end protecting the vector sequence, is generated by digestion with the appropriate combination of endonucleases. The vector with insert is double digested with a) either the first or second Exo III resistant cutter, and b) one of the first set of Exo III sensitive cutters. The cut DNA is then treated with Exo III, which digests one strand of the DNA at the susceptible end (into the insert), in the 3' to 5' direction. The plasmid which is produced has a unidirectional deletion corresponding in size to the amount of Exo III digestion which is allowed to occur.

An alternative method for generating unidirectional deletions in the first terminus of the inserted DNA, is to linearize the plasmid by digestion with the first Exo III resistance cutter, and then to blunt end the resulting overhangs (e.g. by the addition of T4 DNA polymerase and dNTPs) to produce the desired Exo III sensitive end directly adjacent the first terminus, and an intermediate Exo III sensitive end. Digestion of this product with the second Exo III resistance cutter (following inactivation of the T4 DNA polymerase) converts the intermediate Exo III sensitive end into an Exo III resistant end, which protects the vector sequence with an Exo III resistant overhang. The DNA is then treated with Exo III as described directly above for single-stranded 3'–5' digestion into the insert DNA, and then further processed to generate the desired deletion, also described above.

Exo III digestion proceeds synchronously enough that, by stopping the reaction at different times, populations of molecules are produced that have been digested for various distances through the cloned insert. The time of digestion required for a specific length of single-stranded gap, or single-stranded deletion produced by Exo III digestion is determined by empirical experimentation. In preferred embodiments, dNTPs and T4 DNA polymerase are included in the aforementioned ligation reactions to blunt end any ragged ends which may be produced in the deletion process.

The resulting deleted plasmids are transformed into a bacterial host to generate a population of subclones with deletions extending different lengths from one end into the cloned insert. Pooling samples from several different Exo III digestion time points before subsequent Si treatment generates a good distribution of deletion clones following transformation into bacteria. Relative mobility of DNA preparations from these subclones upon agarose gel electrophoresis is used to identify a set in which sequencing each subclone with the same primer (from a site within the flanking vector) generates a set of overlapping sequences that spans the entire insert. Deletion clones are then sequenced using a vector specific primer, the sequence of which can be determined from the sequence listed in FIG. 4. The correctness of the final sequence assembly is verified by correspondence between the position of the sequence from an individual subclone and its size relative to the other subclones, as determined by its relative mobility in agarose gel electrophoresis. This constraint is particularly useful in obtaining correct assemblies of highly repeated sequences.

In a preferred embodiment, *E. coli* D1210 is used as the host for recombinant clones to ensure complete repression of the Pl repL replication origin in the absence of IPTG, since it carries a LacIq allele on the chromosome, whereas most LacIq strains carry this allele on incompatible F' plasmids and therefore cannot be used as hosts for an F-based vector such as pZIP. D1210 is a derivative of the highly transformable strain HB101 which also carries the lacy+ allele on the chromosome which facilitates IPTG uptake.

Another aspect of the present invention is a method for efficient, high-throughput production of complete, highly accurate sequences of full-length cDNAs. The pZIP vector of the present invention has been designed for making normalized full-length cDNA libraries. Tests with human genomic DNA have been successful for cloning fragments as large as 15 kb, well within the range expected for most full-length cDNAs. Promoter sites for SP6, T7, and T3 RNA polymerase flank the cloning region. These sites can be used to synthesize sense or anti-sense RNA, which in turn can be used for library normalization or subtraction. Once a library is produced, unidirectional deletions are generated in the individual clones for high throughput sequencing, by the procedures described above. Although full-length cDNAs in existing cDNA libraries can be transferred to a vector for generating deletions for sequencing, actually generating a cDNA library initially in a vector that is suitable for making deletions is far more efficient.

EXEMPLIFICATION

Section I—Example of Method for Introducing Unidirectional Nested Deletions

Materials

The following reaction buffers were prepared:

I) 10×GeneII buffer 200 mM Tris pH 8.0

800 mM KCl 50 mM DTT ii) 1×Exo III Buffer(USB)

66 mM TrisCl pH 8.0

6.6 mM MgCl 5 mM DTT

50 µg/ml BSA iii) S1 Stop Mix
   0.3 M TrisCl
   50 mM EDTA
iv) 2× Fill-in & Ligation Mix
   40 mM Tris pH 7.6
   20 mM MgCl.
   20 mM DTT
   1.2 mM ATP
   200 μM of each dNTP Methods Double-stranded DNA was nicked by combining the following reagents:
   2 μg DNA (for inserts >20 kb: 4 μg DNA)
   4 μl 10×Gene II Buffer
   2 μl 50 mM MnCl$_2$
   20 μl GeneII serially diluted ⅛

The total reaction volume was brought to 40 μl with the addition of sterile water and the mixture was incubated at 37° C. for 1 hour. The nicked DNA was then phenol extracted and ethanol precipitated. The nicked DNA was then resuspended in 50 μl 1×Exo III Buffer (USB).

2 μl Exo III (200 U, USB) was added to a prewarmed tube containing phenol extracted, nicked DNA. The mixture was incubated at 37° C. 2.5 μl aliquots were sampled at 30 second intervals and mixed with 2.5 μl of S1 nuclease mix (0.5 μl S1 nuclease buffer, 1.25 U S1 nuclease, brought to 2.5 μl with distilled water) on ice. After last time point, all tubes were transferred to 30° C. for 30 minutes. 1 μl of S1 nuclease stop mix was added and the tubes were heated at 70° C. for 10 minutes. 2 μl of each time point was checked by gel electrophoresis. All time points were then combined and ethanol precipitated. The DNA was resuspended in 25 μl Tes1.

To recircularize the deletion-containing DNAs, 25 μl 2× fill-in and ligation mix was added to the above, together with 1 μl T4 DNA ligase (6 Weiss units) and 0.5 μl (2 units) T4 DNA polymerase. The mixture was sonicated at 14 degree C for 10 minutes and incubated at 14° C. overnight. The enzymes were heat-inactivated at 68° C. for 15 minutes, followed by digestion with a restriction enzyme having an uncommon recognition sequence (e.g., PacI or AscI). Following digestion, the DNA was phenol extracted, ethanol precipitated and resuspended in 10 μl sterile water. Cells were then transformed by electroporation with 5 μl DNA and plated on selected antibiotics.

Results

A partial sequence of the human adenovirus receptor gene was determined in the manner described above. A BAC clone containing the human adenovirus receptor gene was purchased from Research Genetics (Huntsville, Ala.). The human DNA insert in this BAC clone is approximately 110 kilobases in length. The BAC DNA was isolated for subcloning by standard techniques. The DNA was digested with the restriction enzyme Bam H1 which yielded approximately 16 fragments. These fragments were individually subcloned into the pND2 vector. All subclones were sequenced in both directions. Nested deletions were performed on 5 of these fragments. In particular, a 10 kb fragment was sequenced completely by the nested deletion strategy. The sequence determined is shown in SEQ ID NO: 1.

Figure 2:
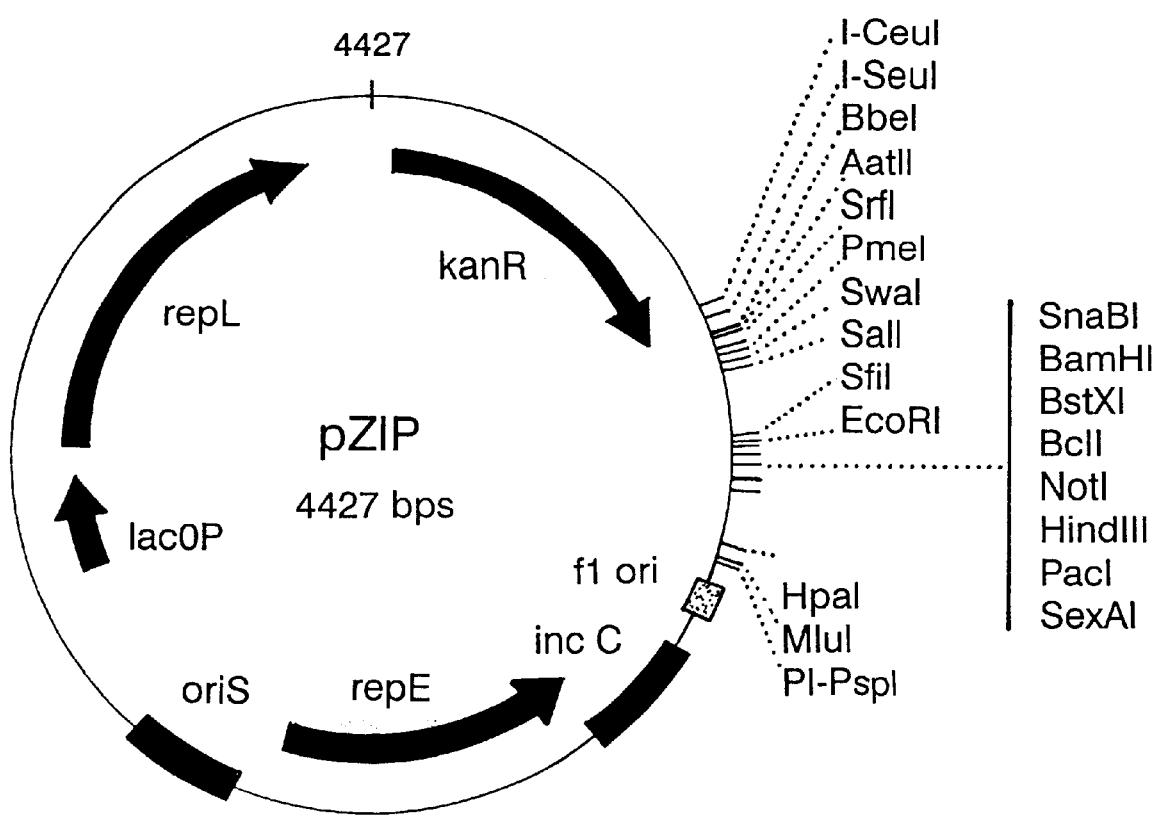
FIG. 2 is a diagrammatic representation of the vector pZIP.
Figure 4:
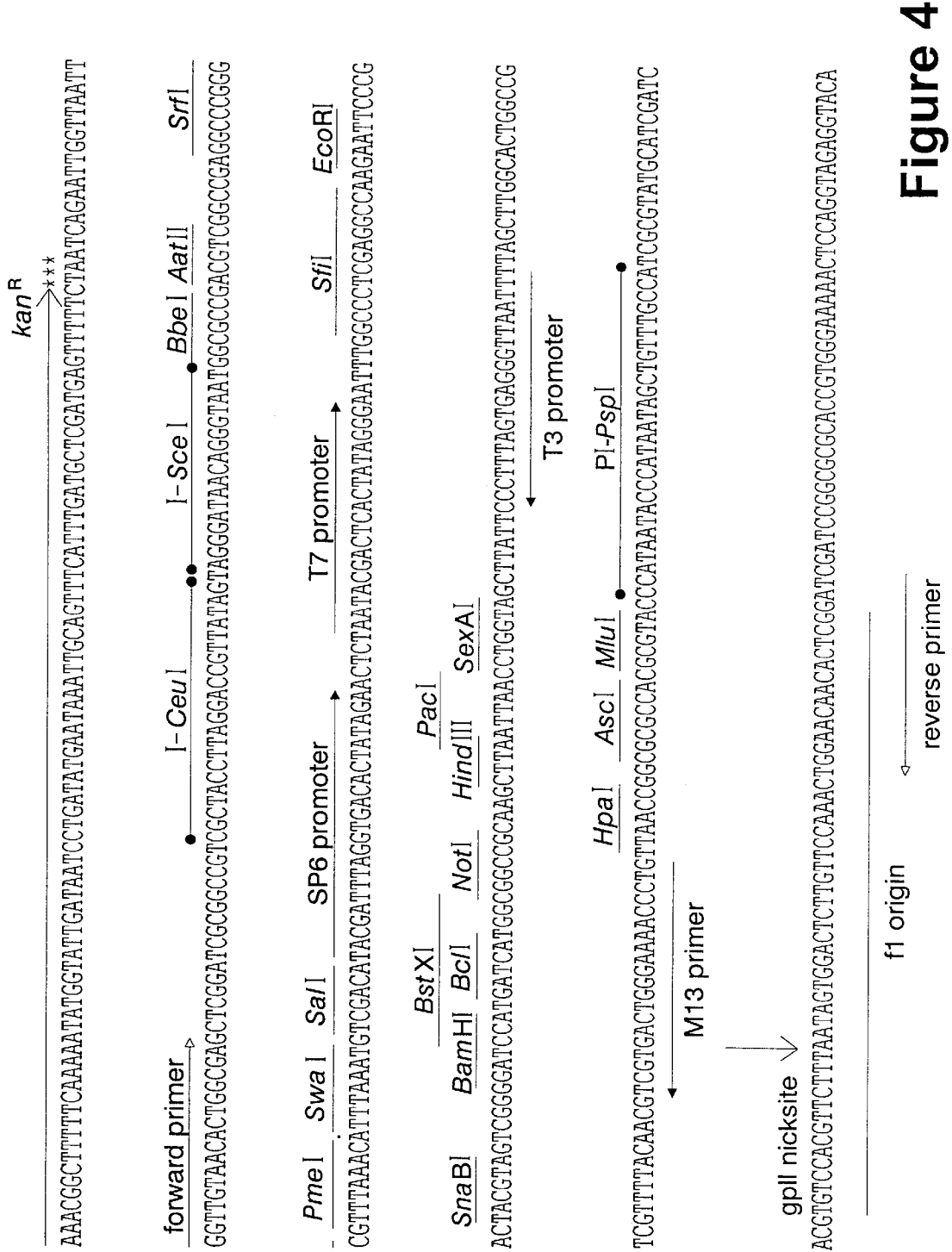
FIG. 4 lists the sequence of one strand (5'–3') of the polylinker region of the pZIP vector, with flanking upstream and downstream sequences SEQ ID NO: 3. The sequence corresponds to nucleotides 733–1332 of the pZIP vector sequence, SEQ ID NO: 2. Specific features encoded by the sequences are indicated.

Section II—Improved Method and Vector for Introducing Unidirectional Nested Deletions The pZIP vector shown in FIG. 2, the sequence of which is listed in FIG. 3 and SEQ ID NO: 2, was constructed to allow rapid generation of ordered sets of nested deletions from either end of a cloned DNA fragment. The size of the vector was reduced to the 4.4-kb range by removing the 2.5-kb sop (stability of plasmid genes) region from the F replicon. The resulting plasmid has a low copy number typical of F plasmids and it remains stable enough to be easily maintained by growth in the presence of the selective antibiotic kanamycin. DNA in amounts convenient for sequencing is readily obtained by amplification from an IPTG-inducible P1 lytic replicon repL (cultures grown in 1 ml 2×YT in 96 deep well plate provide enough DNA for 10–20 sequencing reactions). The vector's multiple cloning region (MCR) has several unique sites for both shotgun and directional cloning (FIG. 4). The MCR was based on the vectors used by Bento Scares (Bonaldo et al., Genome Res. 6(9): 791–806 (1996)) to construct cDNA libraries. It is flanked on one side by recognition sequences for the extremely rare cutting intron encoded nucleases I-CeuI and I-SceI, and on the other side by a recognition sequence for another intron encoded enzyme, PI-PspI, and a nicking site for the phage f1 protein, gpII, that initiates f1 rolling circle DNA replication. Cleavage with the intron encoded enzymes leaves four-base 3' overhangs that are resistant to digestion with E. coli Exo III. Between these sites and the MCR are recognition sites for several rare 8-base cutters that leave Exo III sensitive termini.

Double cutting with one intron encoded enzyme and an adjacent rare cutting restriction endonuclease allows for unidirectional 3' to 5' digestion across the insert with Exo III. Alternatively, plasmid linearized on one side of an insert with I-SceI can be blunt ended to produce an Exo III sensitive end and then cut with I-CeuI to generate an adjacent Exo III resistant end. The f1 nicking site can be used for Exo III digestion of the other strand of the insert or for producing single-stranded plasmid circles for library normalization or subtraction. After Exo III digestion, the resulting single-stranded regions are digested with Si nuclease, and the ends are repaired and ligated with T4 DNA polymerase and ligase. Pooling samples from several different Exo III digestion time points before subsequent S1 treatment generates a good distribution of deletion clones following electroporation. Deletion clones are sized and sequenced using vector specific forward (CCGAGTGTTGTTCCAGTT SEQ ID NO: 4) and reverse (TGGTTGTAACACTGGCGAGC SEQ ID NO: 5) primers, the hybridization positions of which are indicated in FIG. 4. To ensure complete repression of the P1 repL replication origin in the absence of IPTC E. coli D1210 is used as the host for recombinant clones, since it carries a LacIq allele on the chromosome, most LacIq strains carry this allele on incompatible F' plasmids and therefore they can not be used as hosts for the F-based pzip vector. D1210 is a derivative of the highly transformable strain HB101 that also carries the lacy+ allele on the chromosome which facilitates IPTG uptake.

What is claimed is:

1. A DNA cloning vector for generating unidirectional deletions in a cloned insert, comprising:
   a) a cloning region for insertion of a DNA sequence having a first and second terminus;
   b) recognition sequences for a first and a second Exo III resistance cutter adjacently located at discrete positions on a first side of the cloning region, the first Exo III resistance cutter recognition sequence being located between the cloning region and the second Exo III resistance cutter recognition sequence;
   c) recognition sequences for a set of Exo III sensitizing cutters located between the first Exo III resistance cutter recognition sequence and the cloning region; and
   d) an f1 endonuclease recognition sequence adjacently located on the second side of the cloning region.

2. The DNA cloning vector of claim 1 wherein the first and second Exo III resistance cutters are intron encoded endonucleases.

3. The DNA cloning vector of claim 2 wherein the intron encoded endonucleases are selected from the group consisting of I-CeuI, PI-PspI, and I-SceI.

4. The DNA cloning vector of claim 1 wherein one or more of the set of Exo III sensitizing cutters is an endonuclease which has an 8-base recognition sequence.

5. The DNA cloning vector of claim 4 wherein the endonuclease with an 8-base recognition sequence is selected from the group consisting of SrfI, PmeI, and SwaI.

6. The DNA cloning vector of claim 1 which further comprises recognition sequences for a second set of Exo III sensitizing cutters located between the f1 endonuclease recognition sequence and the cloning region.

7. The DNA cloning vector of claim 6 wherein one or more of the second set of Exo III sensitizing cutters is an endonuclease which has an 8-base recognition sequence.

8. The DNA cloning vector of claim 7 wherein the endonuclease with a 8-base recognition sequence of the second set of Exo III sensitizing cutters is selected from the group consisting of NotI, PacI, and AscI.

9. The DNA cloning vector of claim 6 further comprising a recognition sequence for a third Exo III resistance cutter located between the f1 endonuclease recognition sequence and the recognition sequences for the second set of Exo III sensitizing cutters.

10. The DNA cloning vector of claim 1 wherein the cloning region is a multiple cloning region which contains unique restriction sites for shotgun and directional cloning.

11. The DNA cloning vector of claim 10 wherein the cloning region and flanking recognition sequences for Exo III resistance cutters, Exo III sensitizing cutters and f1 comprise the sequence listed in SEQ ID NO: 3.

12. The DNA cloning vector of claim 1 which further comprises one or more sequencing primer binding sites.

13. The DNA cloning vector of claim 1 which is a single-copy vector for generating normalized full-length cDNA libraries.

14. The DNA cloning vector of claim 13 wherein the vector contains a P1 lytic replicon which is under the control of an inducible promoter.

15. The DNA cloning vector of claim 14 wherein the inducible promoter is a Lac promoter which is inducible with IPTG.

16. The DNA cloning vector of claim 13 which is capable of stably propagating a DNA sequence of up to 15 kb in length which is inserted at the cloning region.

17. The DNA cloning vector of claim 16 which is the pZIP vector, the sequence of which is listed in SEQ ID NO: 2.

18. A method for introducing a unidirectional deletion into both termini of a cloned DNA sequence, comprising the steps:

a) providing a recombinant DNA construct comprising a cloning vector for generating nested deletions in a cloned insert, the cloning vector comprising:
  i) a cloning vector for insertion of a cloned DNA sequence, the cloning region having a first and second side;
  ii) recognition sequences for a first and a second Exo III resistance cutter adjacently located at discrete positions on a first side of the cloning region, the first Exo III resistance cutter recognition sequence being located between the cloning region and the second Exo III resistance cutter recognition sequence;
  iii) recognition sequences for a set of Exo III sensitizing cutters located between the first Exo III resistance cutter recognition sequence and the cloning region; and
  iv) an f1 endonuclease recognition sequence adjacently located on the second side of the cloning region, the recombinant DNA construct further comprising a cloned DNA sequence which is inserted into the cloning region of the cloning vector such that the cloned DNA sequence has a first terminus located directly adjacent the first side of the cloning region, and a second terminus located directly adjacent the second side of the cloning region;
b) generating a unidirectional deletion in the first terminus of the cloned DNA sequence by:
  i) linearizing the recombinant DNA construct at a site in the vector located directly adjacent the first terminus of the cloned DNA sequence by digesting the recombinant DNA construct of step a) with endonucleases which generate one Exo III sensitive end, corresponding to the end directly adjacent the first terminus of the cloned DNA sequence, and one Exo III insensitive end;
  ii) digesting the linearized recombinant DNA construct generated in step b)i) with E. coli Exonuclease III, thereby digesting 3' to 5' one strand of the Exo III sensitive end, thereby generating a linearized recombinant DNA construct having a single-stranded deletion in the First terminus of the cloned DNA sequence;
  iii) contacting the linearized recombinant DNA cost ruct generated in step b)ii) with a single-strand-specific endonuclease, thereby generating a DNA molecule containing a double-stranded deletion in the first terminus of the cloned DNA sequence, the deletion corresponding in size to the single-stranded deletion of step b)ii); and
  iv) ligating the DNA molecule generated in step b)iii with DNA ligase, thereby re-circularizing the molecule; and
c) generating a unidirectional deletion in the second terminus of the cloned DNA sequence by:
  i) contacting either the recombinant DNA construct of step a) or the recombinant DNA construct generated in step b)iv) with protein gpII encoded by gene II of phage f1 thereby generating a recombinant DNA construct having a single-stranded nick;
  ii) digesting the recombinant DNA having a single-stranded nick with E. coli Exonuclease III thereby expanding the single-stranded nick into a single-stranded gap, thereby generating a recombinant DNA construct having a single-stranded gap;
  iii) contacting the recombinant DNA construct generated by step c)ii) with a single-strand-specific endonuclease, thereby producing a linearized DNA molecule containing a double-stranded deletion in the cloned DNA of the second terminus, the deletion corresponding in size to the single-stranded gap of step c)ii); and
  iv) ligating the linearized DNA molecule generated by step c)iii) with DNA ligase, thereby recircularizing the molecule.

19. The method of claim 18 wherein the cloning vector of step a) further comprises recognition sequences for a second set of Exo III sensitizing cutters located between the f1 endonuclease recognition sequence and the cloning region, and a recognition sequence for a third Exo III resistance cutter located between the f1 endonuclease recognition sequence and the recognition sequences for the second set of Exo III sensitizing cutters.

20. The method of claim 19 further comprising digesting the recombinant DNA construct generated in step b) with the third Exo III resistance cutter, thereby reducing background from undigested parent DNA constructs.

21. The method of claim 18 wherein the Exo III sensitive end and the Exo III insensitive end of step b)i) are generated by digesting the recombinant DNA construct of step a) with the second Exo III resistance cutter and a member of the first set of Exo III sensitizing cutters.

22. The method of claim 18 wherein the Exo III sensitive end and the Exo III insensitive end of step b)i) are generated by digesting the recombinant DNA construct of step a) with the first Exo III resistance cutter and then blunting the resulting ends thereby generating the Exo III sensitive end of step b)i) and an intermediate Exo III sensitive end, and then further digesting with the second Exo III resistance cutter, thereby converting the intermediate Exo III sensitive end into the Exo III resistant end of step b)i).

23. The method of claim 18 wherein the Exonuclease III digestion of step c)ii) is timed to produce a single-stranded gap having a specific length, the time of digestion required for said specific length being determined by empirical experimentation.

24. The method of claim 18 wherein the Exonuclease III digestion of step b)ii) is timed to produce a single-stranded deletion having a specific length, the time of digestion required for said specific length being determined by empirical experimentation.

25. The method of claim 18 wherein the cloning vector is a single copy cloning vector for generating normalized full-length cDNA libraries.

26. The method of claim 18 wherein the single-strand-specific endonuclease is selected from the group consisting of S1 endonuclease and mung bean endonuclease.

27. The method of claim 26 wherein the single-strand-specific endonuclease is S1 nuclease.

28. The method of claim 18 wherein step c)i) is carried out in a buffer containing the divalent cation $Mn^{2+}$.

29. The method of claim 18 wherein the cloning vector further comprises a sequencing primer binding site.

30. A method for introducing a unidirectional deletion at a terminal location of a cloned DNA sequence, comprising the steps:
  a) providing a recombinant DNA construct comprising a cloning vector for generating nested deletions in a cloned insert, the cloning vector comprising:
    i) a cloning vector for insertion of a cloned DNA sequence, the cloning region having a first and second side;
    ii) recognition sequences for a first and a second Exo III resistance cutter adjacently located at discrete positions on a first side of the cloning region, the first Exo III resistance cutter recognition sequence being locate( between the cloning region and the second Exo III resistance cutter recognition sequence;

iii) recognition sequences for a set of Exo III sensitizing cutters located between the first Exo III resistance cutter recognition sequence and the cloning region; and iv) an f1 endonuclease recognition sequence adjacently located on the second side of the cloning region, the recombinant DNA construct further comprising a cloned DNA sequence which is inserted into the cloning region of the cloning vector such that the cloned DNA sequence has a first terminus located directly adjacent the first side of the cloning region and a second terminus located directly adjacent the second side of the cloning region; and b) generating a unidirectional deletion in the first terminus of the cloned DNA sequence by:

i) linearizing the recombinant DNA construct at a sate in the vector located directly adjacent the first terminus of the cloned DNA sequence, by digesting the recombinant DNA construct of step a) with endonucleases which generate one Exo III sensitive end, corresponding to the end directly adjacent the first terminus of the cloned DNA sequence, and one Exo III insensitive end;

ii) digesting the linearized recombinant DNA construct generated in step b)i) with $E.$ $coli$ Exonuclease III, thereby digesting 3' to 5' one strand of the Exo III sensitive end, thereby generating a linearized recombinant DNA construct having a single-stranded deletion in the first terminus of the cloned DNA sequence;

iii) contacting the linearized recombinant DNA construct generated in step b)ii) with a single-strand-specific endonuclease, thereby generating a DNA molecule containing a double-stranded deletion in the first terminus of the cloned DNA sequence, the deletion corresponding in size to the single-stranded deletion of step b)ii); and iv) ligating the DNA molecule generated in step b) iii) with DNA ligase, thereby re-circularizing the molecule.

31. The method claim 30 wherein the Exo III sensitive end and the Exo III insensitive end of step b)i) are generated by digesting the recombinant DNA construct of step a) with the second Exo III resistance cutter and a member of the first set of Exo III sensitizing cutters.

32. The method of claim 30 wherein the Exo III sensitive end and the Exo III insensitive end of step b)i) are generated by digesting the recombinant DNA construct of step a with the first Exo III resistance cutter and then blunting the resulting ends thereby generating the Exo III sensitive end of step b)i) and an intermediate Exo III sensitive end, and then further digesting with the second Exo III resistance cutter, thereby converting the intermediate Exo III sensitive end into the Exo III resistant end of step b)i).

33. A method for introducing a unidirectional deletion at a terminal location of a cloned DNA sequence, comprising the steps:

a) providing a recombinant DNA construct comprising a cloning vector for generating nested deletions in a cloned Insert, The cloning vector comprising:

i) a cloning vector for insertion of a cloned DNA sequence, the cloning region having a first and second side;

ii) recognition sequences for a first and a second Exo III resistance cutter adjacently located at discrete positions on a first side of the cloning region, the first Exo III resistance cutter recognition sequence being located between the cloning region and the second Exo III resistance cutter recognition sequence;

iii) recognition sequences for a first set of Exo III sensitizing cutters located between the first Exo III resistance cutter recognition sequence and the cloning region;

iv) an f1 endonuclease recognition sequence adjacently located on the second side of the cloning region;

v) recognition sequences for a second set of Exo III sensitizing cutters located between the f1 endonuclease recognition sequence and the cloning region; and vi) a recognition sequence for a third Exo III resistance cutter located between the f1 endonuclease recognition sequence and the recognition sequences for the second set of Exo III sensitizing cutters, the recombinant DNA construct further comprising a cloned DNA sequence which is inserted into the cloning region of the cloning vector such that the cloned DNA sequence has a first terminus located directly adjacent the first side of the cloning region and a second terminus located directly adjacent the second side of the cloning region; and b) generating a unidirectional deletion in the second terminus of the cloned DNA sequence by:

i) digesting the recombinant DNA construct with the third Exo III resistance cutter and with an Exo III sonsitizing cutter from the second set of Exo III sensitizing cutters, thereby generating an Exo III sensitive end and an Exo III resistant end;

ii) digesting the linearized recombinant DNA construct generated by step b)i) with $E.$ $coli$ Exonuclease III, thereby digesting 3' to 5' one strand of the Exo III sensitive end, thereby generating a linearized recombinant UNA construct having a single-stranded deletion in the second terminus of the cloned DNA sequence;

iii) contacting the linearized recombinant DNA construct generated in step b)ii) with a single-strand-specific endonuclease, thereby generating a DNA molecule containing a double-stranded deletion in the second terminus of the cloned DNA sequence, the double-stranded deletion corresponding in size to the single-stranded deletion of step b)ii); and iv) ligating the DNA molecule generated in step b)iii) with DNA ligase, thereby re-circularizing the molecule.

* * * * *

SEQUENCE LISTING

<160> NUMBER OF SEQ ID NOS: 5

<210> SEQ ID NO 1
<211> LENGTH: 10754
<212> TYPE: DNA
<213> ORGANISM: Homo sapiens

<400> SEQUENCE: 1

| | | | | | |
|---|---|---|---|---|---:|
| gatcctcttc | ttcagatgaa | gaaacaagta | aggaaatgga | agtgaaaccc | agttcggtga | 60 |
| ctgcagccgc | aagtcctgtg | taccaggtaa | ccatgaaaac | agctcagttt | taagggatg | 120 |
| tgcagggatt | gccaggacct | ttcaggtagt | cctacttggc | attgcccaag | gtttctgact | 180 |
| tgagattctg | gataatagtt | cttgcctttc | cccatgctaa | gggaaagctg | tttctctggc | 240 |
| acgtaaatag | gcatcctgag | tcattttatc | aaaggtcagc | ttcactatac | aataactagg | 300 |
| ataaatatat | ttcagaaaaa | ttggcaaaaa | gtagaaaatt | catgatggta | aaacattcct | 360 |
| gatattttaa | aatctcattc | aaaagttacc | acttattttt | tgtagtatgt | aacactttgt | 420 |
| tttgtacctt | tgggtttaac | tttctattct | ctcccgttcc | atgattaaag | agaaacctct | 480 |
| ctaaatttat | tatattataa | ttaatatttt | actcaagctg | aaacattgtc | tccctttttg | 540 |
| ctttactagt | tgaaaagtca | tatagctagt | gtgcctgcac | ttacagatcc | attcactgat | 600 |
| ttactattta | tatctacata | ccaaagaaca | tttaatcgac | tttaaaaaat | tgttgaccaa | 660 |
| acagcattct | tcaacaggaa | agatatttta | aagtcataac | aatttaaaga | gattttttga | 720 |
| gttgagcctt | attctgtaaa | tgtacttatt | actaattttt | aaaggttatc | tattttact | 780 |
| tacttgcttt | gattaaatgt | gaaacatacc | aggtttgtgg | taaggttgag | ctgaaaatga | 840 |
| aaatttagac | taatgagtaa | gaagcagaat | attggagctt | ttagtatgat | aaactaaact | 900 |
| tttaaattca | gcatacattt | acataatgaa | cattatttca | gtgtaactta | attttggtt | 960 |
| tctcattttt | ttctcagttg | aattattctt | cctagacttt | aggggaagat | tatttctgaa | 1020 |
| gattatcata | atttaggatt | ctatgtatat | gtgtatgtat | atgtatatgt | atataacatg | 1080 |
| tacctggctt | tatgaaactt | caaacagtac | aagacagtat | aatagtgaga | agtcctcttt | 1140 |
| ctccccaacc | accagtccct | atgcatttcc | acagagacat | tcattaccag | gttttttttt | 1200 |
| cttttttta | gtatccttcc | agagacattc | cctatataaa | taagtaaaca | tagtatttgt | 1260 |
| acttcaggat | catttttaaa | aaccttgcca | taaatatttg | aggcattttt | tttctctgtg | 1320 |
| tgatggatta | tatattgcaa | attaggtata | ttgaattttc | tggaattcat | ccaaatgtgt | 1380 |
| ggcaatttta | cctcagaatt | ttatttgttg | ttaagcaaga | atgtaagtct | caaattaaat | 1440 |
| tgattgctgc | taattttta | caagcaaatt | aacctttaat | ttttaggatt | tcttttaaaa | 1500 |
| ttaaattgca | tttatttcc | ctcatgttga | aagactatta | ggataacaga | aaggtatgga | 1560 |
| aattgaggtg | tctcttacgt | gcttttaag | gaaaacattt | ctccttggcc | taatactcat | 1620 |
| tagcaaaaca | ttttataata | gagaaacact | acttgtgtga | aagctagtgc | aaatggccca | 1680 |
| ctttgatttt | cttctttcta | gtatcttgaa | tctggcattg | ccacaagctt | taaaaaagtt | 1740 |
| ttatcaaata | aggacaacaa | aatttctagc | ttggaatttt | tgttctctac | tgttttctaa | 1800 |
| aaggtatccc | aagagagggg | ataaagaatt | attcatatct | taaaaaacga | agaaatgaag | 1860 |
| attgtgtcag | ttctcctgaa | atagatctgt | agatccaatt | cagtatcaat | gaacatctta | 1920 |
| aaaggttttt | ttctggaaag | tgacaaattg | attcaaaatt | ttaaaaaagg | aggatcagtt | 1980 |
| ggagggctca | cactaattca | aagctattat | atattcatca | agacagtgtg | gtaatggttt | 2040 |

```
aaaaacatac aaatatattg atggcacagg atagagagtc cagaagtaga cccacataca      2100
tacagttagt cttttttctc ccttttaaca aaagtgccaa agcaattcaa tggggaaagt      2160
cttcaagaac ttgtgctgaa acaactggat gatctgtgta ggaaaaaaaa cgaacctaac      2220
ttagctgaca ccatacacaa aaatattgat ttgagatgga ttgtgtacct agacataaaa      2280
gataaatctc tgacgctttt agaagaaaac atagggaaat ataatcttta ttttgtgaca      2340
ggcaaatatt tcctctagag ggtcacaaaa agtaactaat aagggaaaaa aattgacaaa      2400
ctggacttca tcaaaattaa tcatcttttt gttcatcaaa gaaaccatta agaaaatggg      2460
caaaccatag actaggacaa aatattctca ttacatatat ctgtaaagga cttatttcca      2520
gaatatactt tttttaaaat cgctcacaaa tcactagtaa aagtaaatg attcaatgaa       2580 aaataatggg catatcctgc tgtaatctca aaaaagggc aggaggagca aaagatgtga       2640
ataaacactt tacaaaagga gttatgtgaa tggcctcatt tatgatcaga ggaatgcaga      2700
ttaaatccat atgaaaccta gttcttccag aactgcacaa tttaaaagcc tgacagcatg      2760
aaatgttagc aaggatgtga agcagctaga ttcataaact tgctagtcat gtaaaatagt      2820
accactactt tggaaaactg gaactttta acgttaaatg tgtaactctt ctattactca       2880
gcagttccac tcctaagtat taaatattta ccaaaagaaa cgaaaatatg cctataaagc      2940
cttctattag aattaactgt gctgttattc attgcagcat tgttttgttc gttgtgtatc      3000
attgtttttt taatagtaag agactgaaaa cagcctcaat gtcccattac taggagacca      3060
tttaatttat agtcattgct atactatcta gctgtagaaa aatgagaagg atctttatgt      3120
attgatatgt ttctgaaatg tattattatg aaatgtaaaa agcaggatac aatccagtat      3180
acatatatat ttttaagtgt gtatagatgt ggatagaata tctctaaagg tatatttaaa      3240
aaaatgtttg gtgtcagttg cccttgagaa gggttaagat aaagaagata aagggtgaga      3300 taaaaaaga gggactttcc acagtttacc cttttgtact ttttgaattt tctatcatga      3360
atgcaatgct atacacaata taattttttt aaaaaaatcc tatacttaga aatgcagatt      3420
tgagatcagc aaaatcagaa atttaagaag atgtggcatt ctaagcagag aggtctaaaa      3480
ctgctgataa gaacactttg aataatgtga acctgacgtg cccacctgat ttatgggata      3540
atctaaaact attattccca aatactaaac tggctacatc agaatcacct ggggagcttt      3600
gtcaaaatac ctggcctcta gttctgagat tttattattg ttcattagac cagtgctagg      3660
gcatgaatgt tttgtgttta tcttttttt ttctaacttt tattttaggt ttagggatac        3720
acatgaaggt ttgttccata ggtaaacatg tgtcacaggg atttgttgta catattattt      3780
catcacccag gtgtgaagcc cagtactcaa tagttatctt ttctgctcct tttccttctc      3840
ccaccctccc ctctcaaata gactccaatg tctattgttt ccttctttgt gttcataagt      3900
tcttatcatt acctcccact tataagtgag aacatgcggt agttgatttt ctgtttctgc      3960
attagtttgc taaggataat ggcctccagc tccaatgttt tgtatttaaa agcctccaag      4020
tgactcctgg cttagccagc tgtggaaacc actggactaa acaagcatg tccttacaag       4080 cttccattcg ttccatgttt tggtcttttt tggttgaagt tgtttaggaa gtactgtgtt      4140
tgagtttatt catttcttta tgcattcaga aaacattggt cacctgttat acattatacg      4200
cctattacac atgaggtttt taatgtattt agacctgaca ataggagtgt cacttagatg      4260
tgatctcagt gttgtgggta actttgtttg tctttaatga gaaatctgga acatagatga      4320
tgattttttc ctttgaatta acttaatgtg ttctcttccc tacagatttc agaacttata      4380
```

```
tttccacctc ttccaatgtg gcacccttttg cccagaaaaa agccaggaat gtatcgaggg    4440
aatggccatc agaatcacta tcctcctcct gttccatttg gttatccaaa tcagggaaga    4500
aaaaataaac catatcgccc aattccagtg acatgggtac ctcctcctgg aatgcattgt    4560
gaccggaatc actggattaa tcctcacatg ttagcacctc actaacttcg ttttttgattg    4620 tgttggtgtc atgttgagaa aaaggtagaa taaaccttac tacacattaa aagttaaaag    4680
ttcttactaa tagtagtgaa gttagatggg ccaaaccatc aaacttattt ttatagaagt    4740
tattgagaat aatctttctt aaaaaatata tgcactttag atattgatat agtttgagaa    4800
attttattaa agttagtcaa gtgcctaagt ttttaatatt ggacttgagt atttatatat    4860
tgtgcatcaa ctctgttgga tacgagaaca ctgtagaagt ggacgatttg ttctagcacc    4920
tttgagaatt tactttatgg agcgtatgta agttatttat atacaaggaa atctattta    4980 tgtcgttgtt taagagaatt gtgtgaaatc atgtagttgc aaataaaaaa tagtttgagg    5040
catgacaacg cgtgtttctg ttgtgtgcat aaaagggaa aagaacgggt atttcccttc    5100
aatgtattta actaaatagc aaaaacatta aacagaacgt aagaatttta aaatttcctt    5160
tgaaaaatca actattaacc atacttttcc taaaagacca catatcagaa tatgcatatg    5220
aaaagttaaa aatttgttag tggtagttat tgaaaatata ataaaacatc ttttaactat    5280
cagtgtcact atacataggg ttttttaaca aagaatttgg ctcgtactaa ttttgacatg    5340
acatctgact tacatgtcta atgccattgc ataagtaga tgtgttctta cagctgctct    5400
aatctctgtc cttgtgcttt ttttaaaaac atttaagtct ttactagagg cctaaaataa    5460
agtcaaataa tacaatactt cagattcttc agtagtccat atttatacaa ctgtaattcc    5520
atcatcttgt aagggtactt gaactacaaa agaaaaaaa gagatatctc tataagagtt    5580 ttgattttc tccaaaggta aattttttaaa aactaagatc agcaatactt tttccatcac    5640
cttcatcttt aaatttgcag tcttaaatta tttgacttac cagaaaaatc acaacttgct    5700
aataaatcat tgaatgccat ggctattcca caaattattg ttattttttag gaagataaat    5760 tctgttgaaa tacaaaactg cacaaatcat aaaggtatag ctcaatagta tgaaaatgtc    5820 agttttttaaa gtttgcaact tcagaaaact cattttttaaa ccttagagac ttttctagct    5880
ttaatattgt actcttttaag ccatacacaa tttttaacatc tctctaaacc atatctactc    5940
ttttcctgaa atctagtgac tgcctattca aacatgagca tgtttgttta ttagtgtcaa    6000
aagggagatg cgttttatca attttttttta accaaagtta ttgaaagaaa aaaggaaaa    6060 aaaaattact ttcagagtca tcacactgct tccttatggg tccttgagag ttttgtggtg    6120
ataatgacag atttgtaggt gattggcgta aagttggaaa gtttcaagta ttttttatcat    6180 gaagttagca gacagaattt atttattgct ttgcttatga gcaaattggt cctcatctgt    6240 aggttttttca tctgtattta accatgtatg gaaaatactc aaaaattaaa aaaatacaaa    6300
ttttaaaata taactacatt gcattaggta ttatctagat ttaaaggatg tacataggtt    6360
atatgcaaat acgaagccat tttatataag gcacttgagc atctgagatt ttggtatcca    6420
ggaggtcctg gaacaaatcc tccaaggata ctgagggatg actatatagg tttgttggga    6480
aaatcagaag cataatagtg taagaagga agtgttattt ttggcacata cttagtagcc    6540
agaacattcc acgttactac aaaatctcct taattagttt gacgattaaa tgacagggcc    6600
tcttggggaa accactagtt ttgattcaac tgcatacagg tagatgttat tactcataga    6660
agattctgcc agtgtttcga ctacccatcc tccaccttgt cctgaaactt atttagagca    6720
aaagaaagct ctcataaata tggcttttcc aatctattcc taatgaaata aaactgtcac    6780
```

-continued

```
tcagcaactg ggtcttaagt tctagcaagc atggggtaca aaagtttgcc aaacccttt   6840 ttagtagtaa ttatgactct aggtgctttg ttctcttaag tttgtctccc ttagacaact   6900
ccaaggtggt cttaaaacat gactacataa tttcagcttg aaagccttat cgggctattt   6960
caagcaggag tggtttatca ctgaacaata atttgtttaa attctccatt ttattttgt    7020 atttgtaggc ataactgcaa agctctaaat tttataggtt aaacttggat atttgaaaaa   7080
aaaagtttta gtaagttcta tcacattaat actaaagcag tgcttatttc tggtttatta   7140
gtataatatt tatctcaaag tatttaactt tttagtaaac ttctgtggtt ccaagttaag   7200
ataataaagc atttatgttg acttctcact aacagaggta tgtgttaatt tcttatttta   7260
tgattaggaa gagggaaaaa tacaacacct accatgtaca gtttattgtg tagccattct   7320
gtccatttta cagataatag taaataattt ttttaatttt tattactaca tggcaacaac   7380
ttatttaatc atcacagcct caggggtat gtaccattat catcccagtt agataaggat    7440
tccagagaag ttaaaaatgc ccaagatcac agaaaactaa ataatgaagc tctgacttaa   7500
aacccagctg ggctttttta aggcccatgc catggtacct tgccatcaga ttcattttgt   7560
tacctataaa atctaccaaa tcttgaaact tgtaagaagg ttcattatca gaccaagatt   7620 ttttaaaaa aaggaaccat gcgaaggtaa attaatgaga atataagaca ttaaagtatc    7680
tattgattaa ccactaataa atctttggcc aagtttcttg ttacaaacta ctcaatatat   7740
ctgaagaggg agctggctga tcatctgata gtaattttat tgctggaaat agaaattaaa   7800
ttgcaataaa cagtacaacc cagtagagtg aagactgaga tgacaaagca aactgtacca   7860
atgacttgtt acatggaaag atcacacata atgagtagta attcccaagt ctgtcacagt   7920 ctttaactt tttttcttac ttatcagtta cttggcaatt taacagagtg tacaacgtta   7980
gtaaactttg tgccaaattt cttcatatac tctggaatct attgcaatgg atgaagcaat   8040
aacattgtga ggctcttacg gaaacacaac aatatccctg cattgcatat ggcactttat   8100
ggcattgact cgtactgcga agttgtcaca caagcactca tgagcacaag gaaggctca    8160 tgcaattcct ctttaaaata tgtacatttt attcattgca gaaaccatca cccacttcca   8220
aatttaatag cattagtcca tcttctatgt tcctttgttc tttcatgtat acttttaagg   8280
gtaacataag gacaaagtg gaagcatgtt taacccttat caaaaacaaa ttcaccatta    8340
agacttgtag cagatacatc actgcaatta gggtagtttg atgtttattc tgtaaagcac   8400
acaatcagca caaataaaag tactgaattt gtttctccta tcaaaaaaaa aaaaaatacc   8460
tagctacaaa aatttcttcc ataaaagtta agaaacataa tcatgggaga ctttgtgttt   8520
aaatttcata ggacttaaaa atactaatta tgatttagac agcaatgcca tggctaaaaa   8580
atgtttattt gtgtgtatac atatataaaa tttataaaat ataaatccat agggaatatg   8640
ggtgaaacac atttctatct agactagagg tttaatggat catttctgtg tataatatta   8700
gtgttatgac caataaatat atgaacacta atacaaatt aaaacattta ttttgggaat    8760
caaaattaat aatgcccaat attggtgagg gtgtagggga agcagtctct tacagtgtta   8820
ctagaggctt aaagaggagg gcagttacac cttcttgaag tatatatccc ttgatcaagc   8880
aattgtacgt acttctagaa attatctac agaagtactc aaacgaggac cattacctac    8940
gtaataagtg ttcactgcaa aattgttttg ggtggcaaaa ataacaaaag cccaagtagc   9000
caccaataga tgaacagttt aataaaattt gaacatctgt tcaaggaaat gctgtggaaa   9060
ataccatgta gccattaaaa aagagtagaa taaaaaaaaa aatggtatgc ctagaatggt   9120
```

-continued

```
gctagtattg tctgggggca aaaaattgtt aatggtagtt agtgttctca aggcggggaa      9180
tgggacaaat acagagaata ttatttttct actttcaaca ttttgatctt taaattttta      9240
tattgagcat tattactttg taactggagg gtaaaaagac actttctcaa agggctttaa      9300
gacaagttca atggatttat ttttagcaga tgcaaatgct gccatcagtg ataatcaaat      9360
tgtatgtttt gtggacaatc tgttgtattt ctgaattaaa caattgcaat gtggctacag      9420
ttttatgttt gtaatcatac tgtgtctaca aggaaatatt ctgaaatagt aaatacttat      9480 aatgggtag caatagtgca tagtttcctc cagtgttccc attatatata atatgataat       9540
attcatgaga aaaatgttaa atatagtatt tggtgggaga aaacccatt attaagaaaa       9600 agtatttagg gagtagaggg atgcaaaaaa gaaaagtgaa agaaaattta ttaaataccct     9660 tgaaataaa ctttaacaac aacaaaaaag gagtgagtcc tatagagaag aaaattatta      9720
aaatttggtg aaagacaaaa ctgaatagaa gaatatatca tttttaaatg gacctgatat      9780
tataaaagct ttactttct acaaattaat acataaagtc aatagaaatc ataattttaa       9840
aatcccagca aaattttatg taactagaaa gcctgatttt aagtttacat ggaagagtaa      9900
atttcaagaa ttaccaagaa ttgtttttaag taaaacaatg agcagagagt attttttcctt    9960 ttacattatt tattaataca tacttgaagt ataacatagg aataaactaa ttcaccagtg     10020
aaacagaatt acagatccag aaccgaaaca tttatataca gaagtttggt gaatgggct      10080 tttcaaatta aagatgaaga atccactaat caaaaattaa taggtattct tatacaccaa     10140
taacagacaa acagagagcc aaatcatgag tgaactccca ttcacaattg cttcaaagag    10200
aataaaatac ctacgaatcc aacctacaag ggatgtgaag gacctcttca aggagaacta    10260
caaaccactg ctcaatgaaa taaagagga tacaaacaaa cggaagaaca ttccatgctc     10320
atgggtagga agaatcaata tcgtgaaaat ggccatactg cccaaggcaa tttatagatt     10380
caatgccatc cccatcaagc taccaatgac tttcttcaca gaattggaaa aaactacttt    10440
aaagttcata tggaaccaaa aaagagcccg cattgccaac tcaatcctaa gccaaaagaa    10500
caaagctgga ggcatcacac tacctgactt caaactacac tacaagccta cagtaaccaa    10560
aacagcatgg tattggtgcc aaaacagaga tataaaccaa tcgaacagaa cagagccctc   10620
agaaataacg ccacatatct acaactatct gatctttgac aaacctgaga aaacaagca    10680 atggggaaag gattccctat ttaataaatg gtgctgggaa aactggctag ccatatatag    10740
aaagctgaaa ctgg                                                        10754
```

<210> SEQ ID NO 2
<211> LENGTH: 4427
<212> TYPE: DNA
<213> ORGANISM: Artificial Sequence
<220> FEATURE:
<223> OTHER INFORMATION: Description of Artificial Sequence: vector
      sequence

<400> SEQUENCE: 2

```
atgagccata ttcaacggga aacgtcttgc tcgaggccgc gattaaattc caacatggat        60
gctgatttat atgggtataa atgggctcgc gataatgtcg ggcaatcagg tgcgacaatc       120
tatcgattgt atgggaagcc cgatgcgcca gagttgtttc tgaaacatgg caaaggtagc       180
gttgccaatg atgttacaga tgagatggtc agactaaact ggctgacgga atttatgcct      240
cttccgacca tcaagcattt tatccgtact cctgatgatg catggttact caccactgcg       300
atccccggga aaacagcatt ccaggtatta gaagaatatc ctgattcagg tgaaaatatt      360
```

-continued

```
gttgatgcgc tggcagtgtt cctgcgccgg ttgcattcga ttcctgtttg taattgtcct    420
tttaacagcg atcgcgtatt tcgtctcgct caggcgcaat cacgaatgaa taacggtttg    480
gttgatgcga gtgattttga tgacgagcgt aatggctggc ctgttgaaca agtctggaaa    540
gaaatgcata aactgttgcc attctcaccg gattcagtcg tcactcatgg tgatttctca    600
cttgataacc ttatttttga cgaggggaaa ttaataggtt gtattgatgt tggacgagtc    660
ggaatcgcag accgatacca ggatcttgcc atcctatgga actgcctcgg tgagttttct    720
ccttcattac agaaacggct ttttcaaaaa tatggtattg ataatcctga tatgaataaa    780
ttgcagtttc atttgatgct cgatgagttt ttctaatcag aattggttaa ttggttgtaa    840
cactggcgag ctcggatcgc ggccgtcgct accttaggac cgttatagta gggataacag    900
ggtaatggcg ccgacgtcgg ccgaggcccg ggcgtttaaa catttaaatg tcgacatacg    960
atttaggtga cactatagaa ctctaatacg actcactata gggaatttgg ccctcgaggc   1020
caagaattcc cgactacgta gtcggggatc catgatcatg gcggccgcaa gcttaattaa   1080
cctggtagct tattccctt agtgagggtt aatttttagct tggcactggc cgtcgtttta   1140
caacgtcgtg actgggaaaa ccctgttaac cggcgcgcca cgcgtaccca taatacccat   1200
aatagctgtt tgccatcgcg tatgcatcga tcacgtgtcc acgttcttta atagtggact   1260
cttgttccaa actggaacaa cactcggatc gatccggcgc gcaccgtggg aaaaactcca   1320
ggtagaggta cacacgcgga tagccaattc agagtaataa actgtgataa tcaaccctca   1380
tcaatgatga cgaactaacc cccgatatca ggtcacatga cgaagggaaa gagaaggaaa   1440
tcaactgtga caaactgccc tcaaatttgg cttccttaaa aattacagtt caaaaagtat   1500
gagaaaatcc atgcaggctg aaggaaacag caaaactgtg acaaattacc ctcagtaggt   1560
cagaacaaat gtgacgaacc accctcaaat ctgtgacaga taaccctcag actatcctgt   1620
cgtcatggaa gtgatatcgc ggaaggaaaa tacgatatga gtcgtctggc ggcctttctt   1680
tttctcaatg tatgagaggc gcattggagt tctgctgttg atctcattaa cacagacctg   1740
caggaagcgg cggcggaagt caggcatacg ctggtaactt tgaggcagct ggtaacgctc   1800
tatgatccag tcgatttttca gagagacgat gcctgagcca tccggcttac gatactgaca   1860
cagggattcg tataaacgca tggcatacgg attggtgatt tcttttgttt cactaagccg   1920
aaactgcgta aaccggttct gtaacccgat aaagaaggga atgagatatg ggttgatatg   1980
tacactgtaa agccctctgg atggactgtg cgcacgtttg ataaaccaag gaaaagattc   2040
atagcctttt tcatcgccgg catcctcttc agggcgataa aaaaccactt ccttccccgc   2100
gaaactcttc aatgcctgcc gtatatcctt actggcttcc gcagaggtca atccgaatat   2160
ttcagcatat ttagcaacat ggatctcgca gataccgtca tgttcctgta gggtgccatc   2220
agattttctg atctggtcaa cgaacagata cagcatacgt ttttgatccc gggagagact   2280
atatgccgcc tcagtgaggt cgtttgactg gacgattcgc gggctatttt tacgtttctt   2340
gtgattgata accgctgttt ccgccatgac agatccatgt gaagtgtgac aagttttttag   2400 attgtcacac taaataaaaa agagtcaata agcagggata actttgtgaa aaacagctt   2460 cttctgaggg caatttgtca cagggttaag ggcaatttgt cacagacagg actgtcattt   2520
gagggtgatt tgtcacactg aaagggcaat tgtcacaac accttctcta gaaccagcat   2580
ggataaaggc ctacaaggcg ctctaaaaaa gaagatctaa aaactataaa aaaataatt   2640 ataaaaatat cccgtggat aagtggataa ccccaaggga agtttttca ggcatcgtgt   2700 gtaagcagaa tatataagtg ctgttccctg gtgcttcctc gctcactcga aattcccggg   2760
```

```
gatagcttta tgcttgtaaa ccgttttgtg aaaaattttt taaaataaaa aagggggacct    2820 ctagggtccc caattaatta gtaatataat ctattaaagg tcattcaaaa ggtcatccac    2880
cggatcaatt ccccctgctcg cgcaggctgg gtgccaagct ctcgggtaac atcaaggccc    2940
gatccttgga gcccttgccc tcccgcacga tgatcgtgcc gtgatcgaaa tccagatcct    3000
tgacccgcag ttgcaaaccc tcactgatcc gattcattaa tgcagctggc acgacaggtt    3060
tcccgactgg aaagcgggca gtgagcgcaa cgcaattaat gtgagttagc tcactcatta    3120
ggcaccccag gctttacact ttatgcttcc ggctcgtatg ttgtgtggaa ttgtgagcgg    3180
ataacaattt cacacaggaa acagctatga ccatgattac gccaagcgcg gtacctgtcg    3240
cggcaacgcg ctaacagacg tagtaagaac caccagcatt gtaatgctgg ctaaagtcac    3300
tttcctgagc tgtataacga tgagcgattt tacttttttct ggctatgaat tggcctgctt    3360
tgtaacacac tccggtctat cccgtagcgc cgggcatatc ctgtcgcaat gtgcaaatct    3420
cgcggcaaca accagtgaat acttcattca aagcctcac cgcctgatcg cggcagaaac    3480
tggttatagc caatcaaccg tcgttcgtgc attccgtgaa gctgtaaaca aaggtatcct    3540
gtctgtagag attgttatcg gcgatcaccg tgaacgtcgc gctaacctgt accggtttac    3600
accatccttt tggccttcg cacaacaagc caaaaatgcg ctgatagaaa gcaaattaaa    3660
gatctcttca gcggcaacca aggttaaagc tgttctcgct aagacattgg ctttatttaa    3720
ttttttatcc acaccccat gtcaaaatga tacccctcc cctgtcagg atgacgtggc    3780 aataaagaat aagaagtcac aagttaaaaa acaaaaaga tcagtttccg gcggtgccgg    3840
aacaaccagc tcaaaaaat tgacttcatg gatcgctaag gcaaaagcaa aggctgacaa    3900
tctgcggtta tccaaaaaac gcactcaaaa acatgagttc aagcagaaag tagaggcggc    3960
tgcgcggaaa tatgcttacc tgaagaacaa gcgttcgcct gatattggcg ggatatcaaa    4020
cttcgataac ctaccgcatt gcatgacggt aaacgaagct cttaatgcgg ttttagccaa    4080
aaataaagat aacgaacaat ggggtatacc ggcaggattc agagggtaat gaattgctct    4140
aattataacc atgcatactt tcaacacctc tagtttgcca tgaggcaaac tcataggtgt    4200
cctggtaaga ggacactgtt gccaaaactg gacgccccat tattgcaatt aataaacaac    4260
taacggacaa ttctacctaa caataagtgg agttgcggcc ggccgcgatc cgctagcaaa    4320
gccacgttgt gtctcaaaat ctctgatgtt acattgcaca agataaaaat atatcatcat    4380
gaacaataaa actgtctgct tacataaaca gtaatacaag gggtgtt             4427
```

<210> SEQ ID NO 3
<211> LENGTH: 600
<212> TYPE: DNA
<213> ORGANISM: Artificial Sequence
<220> FEATURE:
<223> OTHER INFORMATION: Description of Artificial Sequence: polylinker
      of vector

<400> SEQUENCE: 3

```
aaacggcttt ttcaaaaata tggtattgat aatcctgata tgaataaatt gcagtttcat      60
ttgatgctcg atgagttttt ctaatcagaa ttggttaatt ggttgtaaca ctggcgagct     120
cggatcgcgg ccgtcgctac cttaggaccg ttatagtagg gataacaggg taatggcgcc     180
gacgtcggcc gaggcccggg cgtttaaaca tttaaatgtc gacatacgat ttaggtgaca     240
ctatagaact ctaatacgac tcactatagg gaatttggcc ctcgaggcca agaattcccg     300
actacgtagt cggggatcca tgatcatggc ggccgcaagc ttaattaacc tggtagctta     360
```

-continued

```
ttccctttag tgagggttaa ttttagcttg gcactggccg tcgttttaca acgtcgtgac      420
tgggaaaacc ctgttaaccg gcgcgccacg cgtacccata atacccataa tagctgtttg      480
ccatcgcgta tgcatcgatc acgtgtccac gttctttaat agtggactct tgttccaaac     540
tggaacaaca ctcggatcga tccggcgcgc accgtgggaa aaactccagg tagaggtaca      600

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: sequencing
      primer

<400> SEQUENCE: 4
ccgagtgttg ttccagtt                                                    18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: sequencing
      primer

<400> SEQUENCE: 5
tggttgtaac actggcgagc                                                  20
```